US010612034B2

(12) United States Patent
Schneider et al.

(10) Patent No.: US 10,612,034 B2
(45) Date of Patent: Apr. 7, 2020

(54) PROMOTERS AND TERMINATORS FOR USE IN EUKARYOTIC CELLS

(75) Inventors: Jane C. Schneider, San Diego, CA (US); Bo Liu, San Diego, CA (US); Rekha Seshadri, San Diego, CA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 1481 days.

(21) Appl. No.: 13/486,930

(22) Filed: Jun. 1, 2012

(65) Prior Publication Data

US 2013/0323780 A1 Dec. 5, 2013

(51) Int. Cl.

*C12N 15/85* (2006.01)
*C12N 15/113* (2010.01)
*C12N 15/82* (2006.01)
*C07K 14/405* (2006.01)

(52) U.S. Cl.

CPC ........ *C12N 15/8216* (2013.01); *C07K 14/405* (2013.01); *C12N 15/113* (2013.01)

(58) Field of Classification Search

None

See application file for complete search history.

(56) References Cited

U.S. PATENT DOCUMENTS

| | | | | |
|---|---|---|---|---|
| 5,270,175 | A | 12/1993 | Moll | 435/41 |
| 5,661,017 | A | 8/1997 | Dunahay et al. | 435/172.3 |
| 5,670,367 | A | 9/1997 | Dorner et al. | 435/320.1 |
| 6,027,900 | A | 2/2000 | Allnutt et al. | 435/6 |
| 6,252,140 | B1 | 6/2001 | Mitra et al. | 800/298 |
| 6,316,224 | B1 | 11/2001 | Xia | 435/69.1 |
| 7,084,266 | B1 | 8/2006 | Yanagi et al. | 536/23.7 |
| 7,244,609 | B2 * | 7/2007 | Drocourt | C07K 14/245 435/252.33 |
| 7,642,405 | B2 | 1/2010 | Lee | 800/296 |
| 8,119,859 | B2 | 2/2012 | Vick et al. | 800/293 |
| 2009/0317857 | A1 * | 12/2009 | Vick | C12N 1/12 435/29 |
| 2009/0317904 | A1 | 12/2009 | Vick et al. | 435/320.1 |
| 2010/0210832 | A1 * | 8/2010 | Kilian | C12N 15/79 536/24.1 |
| 2011/0091977 | A1 | 4/2011 | Kilian et al. | 435/471 |
| 2012/0107801 | A1 | 5/2012 | Kilian et al. | 435/6.1 |
| 2012/0208279 | A1 | 8/2012 | Vick et al. | 435/471 |
| 2013/0102040 | A1 * | 4/2013 | Radakovits et al. | 435/134 |

FOREIGN PATENT DOCUMENTS

| | | | |
|---|---|---|---|
| EP | 2 383 337 | 2/2011 | C12N 15/09 |
| WO | WO 2000/062601 | 10/2000 | A01H 13/00 |
| WO | WO-2006/116400 A2 | 11/2006 | |
| WO | WO 2007/133558 | 11/2007 | E21B 37/00 |
| WO | WO 2009/149465 | 12/2009 | |
| WO | WO 2009/149470 | 12/2009 | |

OTHER PUBLICATIONS

Kim et al. A 20 nucleotide upstream element is essential for the nopaline synthase (nos) promoter activity. Plant Molecular Biology. 1994. 24: 105-117.*

Radakovits et al. Draft genome sequence and genetic transformation of the oleaginous alga Nannochloropsis gaditana. Nature Communications. 2012. pp. 1-10.*

GenBank Accession No. JU968567. TSA: Nannochloropsis gaditana CCMP526 NGA_Contig1848. Published May 16, 2012. pp. 1.*

Rombauts et al. PlantCARE, a plant cis-acting regulatory element database. Nucleic Acids Research. 1999. 27(1): 295-296.*

Ross et al. Activation of the Oryza sativa non-symbiotic haemoglobin-2 promoter by the cytokinin-regulated transcription factor, ARR1. Journal of Experimental Biology. 2004. 55(403): 1721-1731.*

Ashikawa. Gene-associated CpG islands in plants as revealed by analyses of genomic sequences. The Plant Journal. 2001. 26(6): 617-625.*

Clontech. 2007. GenomeWalker Universal Kit User Manual. pp. 1-30.*

Gen Bank Accession No. AB052734. Nannochloropsis gaditana chloroplast gene for ribulose-1,5-bisphosphate carbxylase/ oxygenase large subunit, partial cds, strain:MBIC10123. published Aug. 21, 2002. pp. 1.*

Orozco et al. Localization of light-inducible and tissue-specific regions of the spinach bisphosphate carboxylase/oxygenase (rubisco) activase promoter in transgenic tobacco plants. Plant Molecular Biology. 1993. 23: 1129-1138.*

Chen, H., et al. (2008), "Conditional production of a functional fish growth hormone in the transgenic line of nannochloropsis octulata (Eustigmatophyceae)[1]", *J. Phycol.*, 44: 768-776.

Cormack, R., et al. (1997), "Rapid amplification of genomic ends (RAGE) as a simple method to clone flanking genomic DNA" *Gene*, 194: 273-276.

Dent, R., et al. (2005), "Functional genomics of eukaryotic photosynthesis using insertional mutagenesis of *Chlamydomonas reinhardtii*[1]", *Plant Physiology*, 137: 545-556.

EMBL Submission EF178385. Dec. 23, 2006. Retrieved from the internet: <URL:http://www.ebi.ac.uk/Tools/dbfetch/emblfetch?style=html&id=EF178385>. Sequence, nt 6550-5917.

EMBL Submission CU633639. Jan. 8, 2008. Retrieved from the internet: <URL:http://www.ebi.ac.uk/Tools/dbfetch/emblfetch?style=html&id=CU633639&Submit=Go>. Sequence, nt 135192-134946.

(Continued)

*Primary Examiner* — Ashley K Buran

(74) *Attorney, Agent, or Firm* — Harness Dickey & Pierce P.L.C.

(57) ABSTRACT

The present invention provides novel promoter and terminator sequences for use in heterologous gene expression in eukaryotic cells, such as algal cells. The invention further provides expression cassettes comprising a promoter, as described herein, operably linked to a heterologous gene. The invention further provides expression vectors and host eukaryotic cells, such as algal cells, for expressing a protein encoded by the heterologous gene; and methods for identifying promoters.

37 Claims, 4 Drawing Sheets
(4 of 4 Drawing Sheet(s) Filed in Color)
Specification includes a Sequence Listing.

(56) References Cited

OTHER PUBLICATIONS

EMBL Submission CU153385. Oct. 5, 2006. Retrieved from the internet: <URL:http://www.ebi.ac.uk/Tools/dbfetch/emblfetch?style=html&id=CU153385&Submit=Go>. Sequence, nt 605-363.
EMBL Submission EF178346. Dec. 23, 2006. Retrieved from the internet: <URL:http://www.ebi.ac.uk/Tools/dbfetch/emblfetch?style=html&id=EF178346>. Sequence, nt 6968-6461.
EMBL Submission AL065414. May 29, 1999. Retrieved from the internet: <URL:http://www.ebi.ac.uk/Tools/dbfetch/emblfetch?style=html&id=AL065414&Submit=Go>. Sequence, nt 713-1037.
EMBL Submission AC180940. Feb. 2, 2006. Retrieved from the internet: <URL:http://www.ebi.ac.uk/Tools/dbfetch/emblfetch?style=html&id=AL180940&Submit=Go>. Sequence, nt 86693-86812.
EMBL Submission AL108694. Jul. 26, 1999. Retrieved from the internet: <URL:http://www.ebi.ac.uk/Tools/dbfetch/emblfetch?style=html&id=AL108694&Submit=Go>. Sequence, nt 802-944.
Folger, K., et al. (1982), "Patterns of integration of DNA microinjected into cultured mammalian cells: evidence for homologous recombination between injected plasmid DNA molecules", *Molecular and Cellular Biology*, 2(11): 1372-1387.
Gibson, D., et al. (2009), "Enzymatic assembly of DNA molecules up to several hundred kilobases", *Nature Methods*, 6(5): 343-345.
Hallmann, et al., (2006), Swapped green algal promoters: aphVIII-based gene constructs with *Chlamydomonas* flanking sequences work as dominant selectable markers in *Volovox* and vice versa., *Plant Cell Rep*, 25: 582-591.
Hellen, C., et al., (2001), "Internal ribosome entry sites in eukaryotic mRNA molecules", *Genes & Development*, 15:1593-1612.
Henikoff, S., et al. (1992), "Amino acid substitution matrices from protein blocks", *Proc. Natl. Acad. Sci USA*, 89:10915-10919.
International Search Report for PCT/US2012/040541 dated Aug. 31, 2012.
Kim, J., et al., (2011), "High cleavage efficiency of a 2A peptide derived from porcine teschovirus-1 in human cell lines, zebrafish and mice" *PloS One*, 6(4): e18556.
Kindle, K., et al. (1989), "Stable nuclear transformation of chlamydomonas using the chlamydomonas gene for nitrate reductase", *The Journal of Cell Biology*, 109 (6, Part 1), 2589-2601.
Kindle, K., et al. (1990), "High-frequency nuclear transformation of *Chlamydomonas reinhardtii*", *Proc. Natl. Acad. Sci. USA*, 87: 1228-1232.
Komar, A., et al. (2011), "Cellular IRES-mediated translation", *Cell Cycle*, 10(2): 229-240.
Lumbreras, V., et al., (1998), "Efficient foreign gene expression in *Chlamydomonas reinhardtii* mediated by an endogenous intron", *The Plant Journal*, 14(4): 441-447.
Méndez-Alvarez, S., et al. (1994), "Transformation of chlorobium limicola by a plasmid that confers the ability to utilize thiosulfate" *Journal of Bacteriology*,176(23):7395-7397.
Mortazavi, A., et al. (2008), "Mapping and quantifying mammalian transcriptomes by RNA-Seq", *Nature Methods*, 5(7): 621-628.
Ohnuma M., et al. (2008), "Polyethylene glycol (PEG)-mediated transient gene expression in a red alga, cyanidioschyzon merolae 10D", *Plant Cell Physiol.* 49(1):117-120.
Pearson W., et al. (1988), "Improved tools for biological sequence comparison" *Proc. Natl. Acad. Sci. USA*, 85:2444-2448.
Perrone, C., et al. (1998), "The chlamydomonas IDA7 locus encodes a 140 kDa dynein intermediate chain required to assemble the I1 inner arm complex", *Molecular biology of the Cell*, 9:3351-3365.
Reeder, R., et al. (1997), "Terminating transcription in eukaryotes: lessons learned from RNA polymerase I", *Trends Biochem Sci.*, 22: 473-477.
Schneider, M., et al. (2005), "Genotyping of transgenic mice: old principles and recent developments", *Analytical Biochemistry*, 344: 1-7.
Walker, T., et al. (2005), "characterization of the *Dunaliella teritiolecta* RbcS genes and their promoter activity in *Chlamydomonas reinhardtii*", *Plant Cell Reports*, 23: 727-735.
Wijffels, R., et al., (2010), "An outlook on microalgal biofuels", *Science Magazine*, 329(5993): 796-799.
Wolk, P., et al. (1984), "Construction of shuttle vectors capable of conjugative transfer from *Escherichia coli* to nitrogen-fixing filamentous cyanobacteria", *Proc. Natl. Acad. Sci. USA*, 81: 1561-1565.
International Preliminary Report on Patentability dated Dec. 2, 2014 issued in PCT Patent Application No. PCT/US2012/040541.
Database Accession No. JU963026, created May 17, 2012, "ISA: Nannochloropsis Gaditana CCMP526 NGA_Contig35297 mRNA sequence".
Database Accession No. JU978110, created May 17, 2012, "ISA: Nannochloropsis Gaditana CCMP526 NGA_Contig16857 mRNA sequence".
European Search Report dated Oct. 2, 2015 issued in European Patent Application No. 12877919.6.
Lissemore, J., et al. (2000), "Green Fluorescent Protein as a Quantitative Reporter of Relative Promoter Activity in *E. coli*", *Biotechniques*, 28(1): 82-89.
Brazilian Office Action dated Jul. 30, 2019 issued in Brazilian Patent Application No. BR112014029799-1 (with English translation), 5 pages.

* cited by examiner

Oneway Analysis of RFP/10^7cells By Plasmid

Means and Std Deviations

| Level | Number | Mean | Std Dev | Std Err Mean | Lower 95% | Upper 95% |
|---|---|---|---|---|---|---|
| pSGE05133 | 4 | 225.296 | 50.555 | 25.28 | 144.85 | 305.74 |
| pSGE05134 | 4 | 75.692 | 7.469 | 3.73 | 63.81 | 87.58 |
| pSGE05136 | 4 | 499.842 | 104.087 | 52.04 | 334.22 | 665.47 |
| pSGE05138 | 4 | 280.451 | 157.176 | 78.59 | 30.35 | 530.55 |
| pSGE05140 | 4 | 532.085 | 274.757 | 137.38 | 94.89 | 969.28 |
| WT | 1 | 11.115 | . | . | . | . |

PROMOTERS AND TERMINATORS FOR USE IN EUKARYOTIC CELLS

FIELD

The present invention relates to gene regulatory elements for use in heterologous gene expression in eukaryotic cells, particularly algal cells.

BACKGROUND

Algal cells are a promising source of biofuels (Wijffels & Barbosa (2010) *Science* 329:796-799). Their ability to harness solar energy to convert carbon dioxide into carbon-rich lipids already exceeds the abilities of oil-producing agricultural crops, with the added advantage that algae grown for biofuel do not compete with oil-producing crops for agricultural land (Wijffels & Barbosa, 2010). In order to maximize algal fuel production, new algal strains will need to be engineered for growth and carbon fixation at an industrial scale (Wijffels & Barbosa, 2010). One engineering method is to create stable expression of heterologous genes which requires the use of gene regulatory elements such as promoters and terminators. The identification of feasible regulatory elements is important to drive optimal expression of genes relating to biofuel production in recombinant algae.

Investigators have begun to identify regulatory sequences for biofuel production. To date, much of this work has focused on inducible promoters that can be activated and deactivated by the application of environmental stimuli Vick & Killian, for instance, report a *Nannochloropsis oceanica* vcp promoter sequence, which is regulated by light-exposure, to drive ectopic gene expression in *N. oceanica* (U.S. 2009/317,904).

U.S. Pat. No. 6,027,900 to Allnut et al. reports a light-responsive fcpA promoter from *Phœodactylum tricornutum* to drive ectopic gene expression in *P. tricornutum.*

U.S. Pat. No. 5,661,017 to Dunahay et al. reports a sterol-responsive acc promoter from *Cyclotella cryptica* to drive ectopic gene expression in *Cyclotella* and *Navicula* species.

U.S. Pat. No. 7,642,405 to Lee reports anaerobically inducible promoters like the hyd1 promoter from *Chlamydomonas reinhardtii* and nitrate-regulated promoters like nial from *C. reinhardtii* to drive ectopic gene expression in *C. reinhardtii.*

U.S. Pat. No. 6,252,140 to Mitra et al. reports inducible *Chlorella* virus promoters to drive ectopic gene expression in *Escherichia coli*, wheat, rice, tobacco, and *Arabidopsis thaliana.*

U.S. Pat. No. 6,316,224 to Xia reports inducible *Chlorella* virus promoters to drive ectopic gene expression in *E. coli*, tobacco, and wheat.

By contrast, fewer investigators have reported the discovery of constitutively active promoters to drive ectopic gene expression in algae. U.S. Pat. No. 5,270,175 to Moll reports the use of RuBisCo small subunit (ssu) promoters to drive ectopic gene expression of yeast fermentation enzymes in *Ulva* species.

Walker et al. (2004) *Plant Cell Reports* 23:727-735 report RuBisCo promoters and terminators from *Dunaliella tertiolecta* to drive gene expression in *C. reinhardtii.*

Chen et al. (2008) *J. Phycol.* 44:768-776 report RuBisCo promoters from *C. reinhardtii* to drive ectopic gene expression in *Nannochloropsis oculata*. There is, therefore, a comparative lack of knowledge relating to promoters and terminators suitable for driving constitutive gene expression in *Nannochloropsis* species, particularly of constitutive promoters and terminators derived from *Nannochloropsis* species.

SUMMARY

This section provides a general summary of the disclosure, and is not a comprehensive disclosure of its full scope or all of its features.

In one aspect, an isolated DNA molecule is provided in which the isolated DNA molecule comprises a sequence selected from the group consisting of a nucleotide sequence having at least 80% identity to at least 100 contiguous nucleotides of SEQ ID NO:1; a nucleotide sequence having at least 80% identity to at least 100 contiguous nucleotides of SEQ ID NO:3; a nucleotide sequence having at least 80% identity to at least 100 contiguous nucleotides of SEQ ID NO:5; a nucleotide sequence having at least 80% identity to at least 100 contiguous nucleotides of SEQ ID NO:7; and a nucleotide sequence having at least 80% identity to at least 100 contiguous nucleotides of SEQ ID NO:9.

For example, an isolated DNA molecule as provided herein can include any or any combination of: a nucleic acid sequence that has at least 85% or at least 90% nucleotide sequence identity to at least 100 contiguous nucleotides of SEQ ID NO:1, a nucleic acid sequence that has at least 85% or at least 90% nucleotide sequence identity to at least 100 contiguous nucleotides of SEQ ID NO:3, a nucleic acid sequence that has at least 85% or at least 90% nucleotide sequence identity to at least 100 contiguous nucleotides of SEQ ID NO:5, a nucleic acid sequence that has at least 85% or at least 90% nucleotide sequence identity to at least 100 contiguous nucleotides of SEQ ID NO:7, or a nucleic acid sequence that has at least 85% or at least 90% nucleotide sequence identity to at least 100 contiguous nucleotides of SEQ ID NO:9. In some examples, an isolated DNA molecule can include a nucleic acid sequence that has at least 95% identity to at least 100 contiguous nucleotides of SEQ ID NO:1, a nucleic acid sequence that has at least 95% identity to at least 100 contiguous nucleotides of SEQ ID NO:3, a nucleic acid sequence that has at least 95% identity to at least 100 contiguous nucleotides of SEQ ID NO:5, a nucleic acid sequence that has at least 95% identity to at least 100 contiguous nucleotides of SEQ ID NO:7, or a nucleic acid sequence that has at least 95% identity to at least 100 contiguous nucleotides of SEQ ID NO:9. In some examples an isolated DNA molecule as provided herein can be selected from the group consisting of: an isolated DNA molecule that comprises a nucleotide sequence comprising at least 100 contiguous nucleotides of SEQ ID NO:1; an isolated DNA molecule that comprises a nucleotide sequence comprising at least 100 contiguous nucleotides of SEQ ID NO:3; an isolated DNA molecule that comprises a nucleotide sequence comprising at least 100 contiguous nucleotides of SEQ ID NO:5; an isolated DNA molecule that comprises a nucleotide sequence comprising at least 100 contiguous nucleotides of SEQ ID NO:7; and an isolated DNA molecule that comprises a nucleotide sequence comprising at least 100 contiguous nucleotides of SEQ ID NO:9.

For example, an isolated DNA molecule as provided herein can comprise a nucleotide sequence having at least 95% sequence identity to at least 100, at least 200, at least 300, at least 400, or at least 500 contiguous nucleotides of SEQ ID NO:1; a nucleotide sequence having at least 95% sequence identity to at least 100, at least 200, at least 300, at least 400, or at least 500 contiguous nucleotides of SEQ ID NO:3; a nucleotide sequence having at least 95% sequence identity to at least 100, at least 200, at least 300, at least 400, or at least 500 contiguous nucleotides of SEQ ID NO:5; a nucleotide sequence having at least 95% sequence identity to at least 100, at least 200, at least 300, at least 400, or at least 500 contiguous nucleotides of SEQ ID NO:7; or a nucleotide sequence having at least 95% sequence identity to at least 100, at least 200, at least 300, at least 400, or at least 500 contiguous nucleotides of SEQ ID NO:9. An isolated DNA molecule as disclosed herein can find use, for example, as a sequence that when operably linked to a nucleic acid sequence encoding a polypeptide or functional RNA can affect expression of the nucleic acid sequence encoding a polypeptide or functional RNA.

Also provided herein is a promoter comprising a nucleic acid sequence having at least 80% identity to at least 100 contiguous nucleotides of SEQ ID NO:1, SEQ ID NO:3, SEQ ID NO:5, SEQ ID NO:7, or SEQ ID NO:9. For example, a promoter as provided herein can comprise a nucleic acid sequence having at least 85% or at least 90% sequence identity to at least 100 contiguous nucleotides of SEQ ID NO:1, at least 100 contiguous nucleotides of SEQ ID NO:3, at least 100 contiguous nucleotides of SEQ ID NO:5, at least 100 contiguous nucleotides of SEQ ID NO:7, or at least 100 contiguous nucleotides of SEQ ID NO:9. In some examples, a promoter can have at least 95% identity to at least 100 contiguous nucleotides of SEQ ID NO:1, at least 100 contiguous nucleotides of SEQ ID NO:3, at least 100 contiguous nucleotides of SEQ ID NO:5, at least 100 contiguous nucleotides of SEQ ID NO:7, or at least 100 contiguous nucleotides of SEQ ID NO:9. In various examples, a promoter as provided herein can comprise a nucleic acid sequence having at least 85%, or at least 90%, or at least 95% identity to at least 200, at least 300, at least 400, or at least 500 contiguous nucleotides of SEQ ID NO:1, SEQ ID NO:3, SEQ ID NO:5, SEQ ID NO:7, or SEQ ID NO:9.

For example, a promoter can comprise a nucleic acid sequence that includes at least 100, at least 200, at least 300, at least 400, or at least 500 contiguous nucleotides of SEQ ID NO:1; at least 100, at least 200, at least 300, at least 400, or at least 500 contiguous nucleotides of SEQ ID NO:3; at least 100, at least 200, at least 300, at least 400, or at least 500 contiguous nucleotides of SEQ ID NO:5; at least 100, at least 200, at least 300, at least 400, or at least 500 contiguous nucleotides of SEQ ID NO:7; or at least 100, at least 200, at least 300, at least 400, or at least 500 contiguous nucleotides of SEQ ID NO:9. For example, a promoter as provided herein can be selected from the group consisting of SEQ ID NO:1; SEQ ID NO:3; SEQ ID NO:5; SEQ ID NO:7; and SEQ ID NO:9.

A promoter as provided herein can be a constitutive promoter, and may be active in a host cell cultured under conditions in which one or more nutrients are deficient as well as in culture conditions in which nutrients are sufficient for proliferation and/or growth of the culture. For example, a promoter provided herein may mediate transcriptions of an operably linked nucleic acid sequence in nitrogen replete as well as in nitrogen limiting conditions.

Also provided is an isolated DNA molecule comprising a sequence selected from the group consisting of a nucleotide sequence having at least 80% identity to at least 100 contiguous nucleotides of SEQ ID NO:2; a nucleotide sequence having at least 80% identity to at least 100 contiguous nucleotides of SEQ ID NO:4; a nucleotide sequence having at least 80% identity to at least 100 contiguous nucleotides of SEQ ID NO:6; a nucleotide sequence having at least 80% identity to at least 100 contiguous nucleotides of SEQ ID NO:8; and a nucleotide sequence having at least 80% identity to at least 100 contiguous nucleotides of SEQ ID NO:10. For example, an isolated DNA molecule can comprise a nucleotide sequence having at least 85% or at least 90% to at least 100 contiguous nucleotides of SEQ ID NO:2, SEQ ID NO:4, SEQ ID NO:6, SEQ ID NO:8, or SEQ ID NO:10. In some examples, an isolated DNA molecule can have at least 95% to at least 100 contiguous nucleotides of SEQ ID NO:2, SEQ ID NO:4, SEQ ID NO:6, SEQ ID NO:8, or SEQ ID NO:10. For example, an isolated DNA molecule as provided herein can be selected from the group consisting of an isolated DNA molecule comprising at least 100, at least 200, at least 300, at least 400, or at least 500 contiguous nucleotides of SEQ ID NO:2; an isolated DNA molecule comprising at least 100, at least 200, at least 300, or at least 400 contiguous nucleotides of SEQ ID NO:4; a nucleotide sequence comprising at least 100, at least 150, or at least 175 contiguous nucleotides of SEQ ID NO:6; a nucleotide sequence comprising at least 100, at least 200, or at least 300 contiguous nucleotides of SEQ ID NO:8; and a nucleotide sequence comprising at least 100, at least 200, or at least 300 contiguous nucleotides of SEQ ID NO:10. The isolated DNA molecule can comprise a terminator. The DNA molecule can find use, for example, as a sequence that when operably linked to a nucleic acid sequence encoding a polypeptide or functional RNA can affect expression of the nucleic acid sequence encoding a polypeptide or functional RNA.

Also provided herein is an expression cassette. The expression cassette comprises a promoter as disclosed herein and a heterologous gene operably linked to the promoter. The gene can encode, for example, a polypeptide or a functional RNA. The expression cassette can further optionally comprise a nucleic acid sequence comprising a terminator sequence, such as but not limited to, any disclosed herein. In various examples, the expression cassette can include a heterologous gene that encodes (a) protein associated with lipid biosynthesis, (b) a lipase, (c) a protein that participates in photosynthesis, (d) a protein associated with carbon fixation, (e) a transporter protein, (f) a dehydrogenase, (g) a transcription factor, (h) a protein involved in cell signaling, or (i) a functional RNA. A functional RNA can be selected from the group consisting of an antisense sequence, a micro RNA, a shRNA, and a ribozyme. The expression cassette can be provided in a vector, e.g., an expression vector, that can optionally include one or more of an origin of replication, sequences mediating recombination into a host genome, or a selectable marker.

Further provided is an expression cassette that includes a promoter as provided herein operably linked to a selectable marker gene or reporter gene. For example, an expression cassette can include a promoter as disclosed herein operably linked to a gene encoding a fluorescent protein and in particular nonlimiting examples can comprise any of SEQ ID NO:12, SEQ ID NO:13, SEQ ID NO:14, SEQ ID NO:15 or SEQ ID NO:16.

Further provided herein is a vector for eukaryotic cell transformation that comprises an expression cassette in which a promoter as disclosed herein is operably linked to a selectable marker gene or reporter gene. The transformation vector can further include a terminator, such as but not limited to any disclosed herein, operably linked to the selectable marker or reporter gene coding sequence. The gene encoding a selectable marker can be a gene encoding a polypeptide that confers resistance to an antibiotic, a polypeptide that confers tolerance to an herbicide, a gene encoding an auxotrophic marker, or any other gene product that can allow for selection of tranformants. A gene encoding a reporter gene can, for example, encode a fluorescent protein or an enzyme that can produce a detectable product.

In another embodiment, a method for transforming a eukaryotic cell is provided. The method comprises introducing the transformation vector that includes a promoter as provided herein operably linked to a selectable marker and selecting for a transformant. The eukaryotic cell can be selected from the group consisting of fungi, heterokonts, algae, and plants, and in a particular embodiment is an algal cell.

For example, an algal cell that can be transformed with a vector as provided herein can be selected from the group consisting of species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*. For example, the algal cell can be a *Nannochloropsis* cell or an *Ellipsoidon* cell.

Also provided is a eukaryotic host cell transformed with an expression vector or transformation vector as provided herein. The eukaryotic host cell can be a microorganism such as a heterokont or microalga, such as but not limited to for example, a *Nannochloropsis* cell or an *Ellipsoidon* cell.

Further, the invention provides a method for detecting promoter activity in an algal cell. The method comprises transforming an algal cell culture with an expression vector that includes a) an expression cassette that comprises a known or putative promoter sequence operably linked to a gene encoding a fluorescent protein, and b) a selectable marker gene, to produce a transformation culture; selecting transformed cells on agar containing a selection agent such that transformed cells form colonies; and measuring fluorescent protein signal(s) produced by one or more algal colonies to identify at least one algal colony that includes an expression vector that comprises an active promoter. Optionally, the putative promoter sequence can be derived from the nuclear genome of an algal species. Further optionally, the agar can include nitrogen replete media, and the methods can be used to identify promoters that may be active under nitrogen replete conditions. The transformation culture may optionally be analyzed by flow cytometry before selecting transformed cells.

The method can further comprise, prior to transforming, cloning a putative promoter sequence and a gene encoding a fluorescent protein into an expression vector that includes a selectable marker gene such that the putative promoter sequence is upstream of the fluorescent protein gene.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings described herein are for illustrative purposes only of selected embodiments and not all possible implementations, and are not intended to limit the scope of the present disclosure.

DETAILED DESCRIPTION

Figure 1:
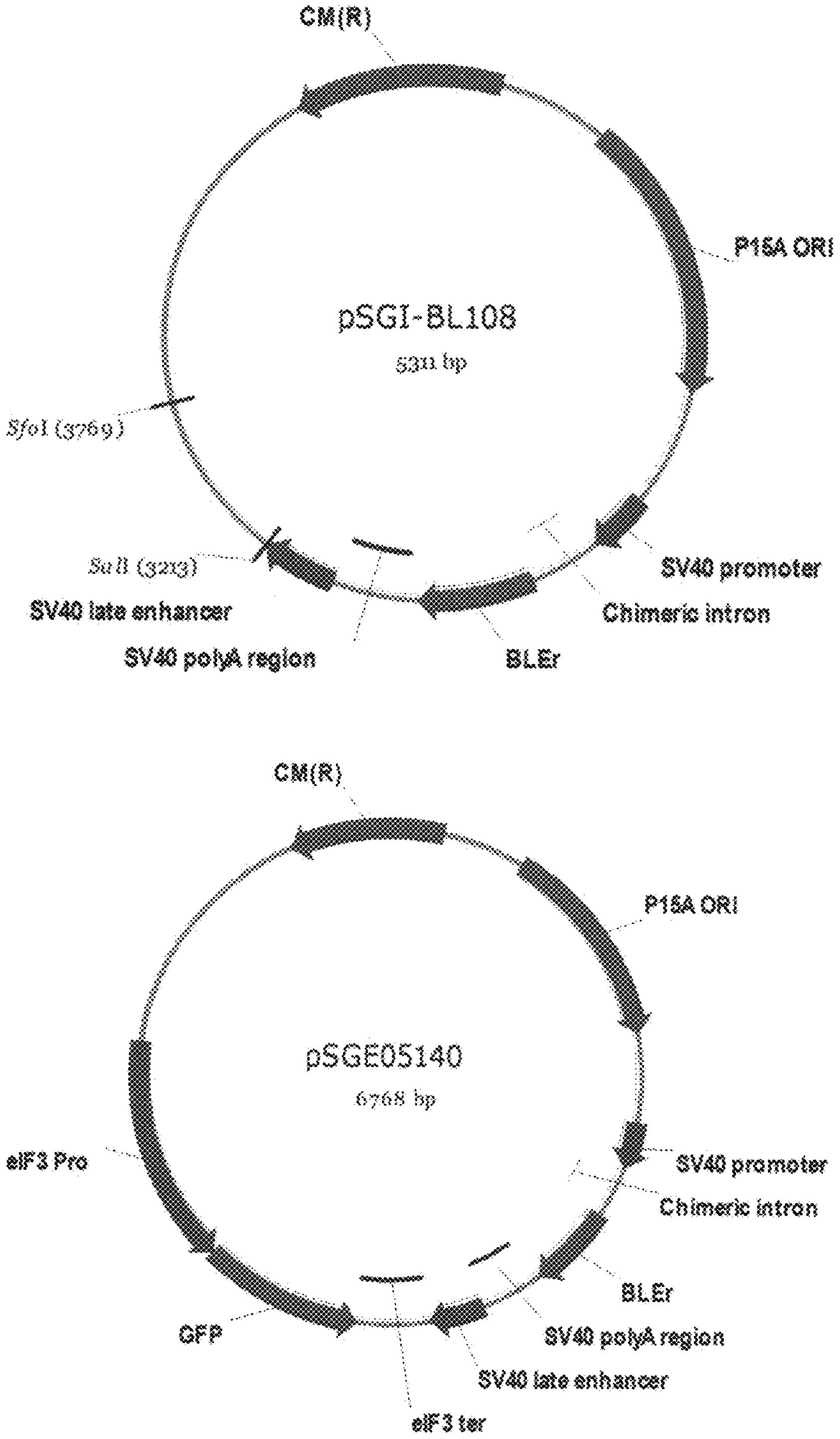
FIG. 1 is a plasmid map for p108 and p05140.

Stable expression of heterologous genes requires the use of gene regulatory elements such as promoters and terminators. Novel promoters and terminators for use in driving heterologous gene expression in eukaryotic species such as heterokont and microalgal species, including *Nannochloropsis*, are provided herein. Transformed heterokont or algal cells can be used, for example, for synthesis of various products including lipids.

A. Definitions

The terms, "cells", "cell cultures", "cell line", "recombinant host cells", "recipient cells" and "host cells" as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

The term "gene" is used broadly to refer to any segment of nucleic acid molecule (typically DNA, but optionally RNA) encoding a protein or expressed RNA. Thus, genes include sequences encoding expressed RNA (which can include polypeptide coding sequences as well as functional RNA sequences). Genes may further comprise the regulatory sequences required for their expression. Genes can be obtained from a variety of sources, including cloning from a source of interest or synthesizing from known or predicted sequence information, and may include sequences designed to have desired parameters.

The terms, "coding sequence" or "coding region" as used herein, refer to regions of a nucleic acid sequence which can be transcribed to produce a functional RNA or an RNA transcript that can be translated into a polypeptide when placed under the control of appropriate expression control sequences and in the presence of appropriate cellular machinery or enzymes. The term "non-coding sequence" or "non-coding region" refers to regions of a nucleic acid sequence that are not transcribed and translated into amino acids (e.g., untranslated regions, signal sequences, etc.) or functional RNA sequences.

A "functional RNA molecule" is an RNA molecule that can interact with one or more proteins or nucleic acid molecules to perform or participate in a structural, catalytic or regulatory function that affects the expression or activity of a gene or gene product other than the gene that produced the functional RNA. A functional RNA can be, for example, a transfer RNA (tRNA), ribosomal RNA (rRNA), anti-sense RNA (asRNA), microRNA (miRNA), short-hairpin RNA (shRNA), small interfering RNA (siRNA), small nucleolar RNAs (snoRNAs), piwi-interacting RNA (piRNA), or a ribozyme.

"Regulatory sequence", "regulatory element", or "regulatory element sequence" refers to a nucleotide sequence located upstream (5'), within, or downstream (3') of a coding sequence. Transcription of the coding sequence and/or translation of an RNA molecule resulting from transcription of the coding sequence is typically affected by the presence or absence of the regulatory sequence. These regulatory element sequences may comprise promoters, cis-elements, enhancers, terminators, or introns. Regulatory elements may be isolated or identified from UnTranslated Regions (UTRs) from a particular polynucleotide sequence. Any of the regulatory elements described herein may be present in a chimeric or hybrid regulatory expression element. Any of the regulatory elements described herein may be present in a recombinant construct of the present invention.

The terms "promoter," "promoter region," or "promoter sequence" refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked transcribable polynucleotide molecule, e.g., a coding sequence. Promoters may contain, in addition to sequences recognized by RNA polymerase and, preferably, other transcription factors, regulatory sequence elements such as cis-elements or enhancer domains that effect the transcription of operably linked genes. An "algal promoter" is a native or non-native promoter that is functional in algal cells. Similarly, a "heterokont promoter" is a native or non-native promoter that is functional in heterokont (stramenopile) cells.

The term, "constitutive" promoter as used herein, refers to a promoter that is active under most environmental and developmental conditions. A constitutive promoter is active regardless of external environment, such as light and medium. In some examples, a constitutive promoter is active in the presence and in the absence of a nutrient. For example, a constitutive promoter may be a promoter that is active (mediates transcription of a gene to which it is operably-linked) under conditions of nitrogen depletion as well as under conditions in which nitrogen is not limiting (nitrogen replete conditions). In contrast, an "inducible" promoter is a promoter that is active in response to particular environmental conditions, such as the presence or absence of a nutrient or regulator, the presence of light, etc.

A nucleic acid molecule may be "derived from" an indicated source, which includes the isolation (in whole or in part) of a nucleic acid segment from an indicated source or the purification of a polypeptide from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can incur one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis. A gene or nucleic acid molecule that is derived from a referenced gene or nucleic acid molecule that encodes a functional RNA or polypeptide can encode a functional RNA or polypeptide having at least 70%, at least 75%, at least 80%, at least 85%, at least 90%, at least 95%, at least 96%, at least 97%, at least 98%, or at least 99% sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

The term, "isolated" biomolecule, such as an isolated protein or nucleic acid as used herein, refers to a biomolecule removed from the context in which the biomolecule exists in nature. An isolated biomolecule can be, in some instances, partially or substantially purified. For example, an isolated nucleic acid molecule can be a nucleic acid sequence that has been excised from the chromosome, genome, or episome into which it is integrated in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

The terms "naturally-occurring" and "wild-type" (WT) refer to a form found in nature. For example, a naturally occurring or wild-type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, insertional mutation, or meganuclease disruption) or having decreased expression due to alteration of gene regulatory sequences. An attenuated gene may also be a gene that is targeted by a "gene knockdown" construct, such as, for example, a construct encoding an antisense RNA, a micro-RNA, a short hairpin RNA, or a ribozyme, for example. In the case of both expression of transgenes and suppression of endogenous genes (e.g., by antisense or sense suppression) one of ordinary skill will recognize that the inserted polynucleotide sequence need not be identical, but may be only substantially identical to a sequence of the gene from which it was derived. As explained herein, these substantially identical variants are specifically covered by reference to a specific nucleic acid sequence.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and may in this context be described as "heterologous" with respect to the host organism), or from the same species (and so may in this context be described as "homologous" with respect to the host organism), relative to the cell being transformed. An "endogenous" nucleic acid molecule, gene or protein is a native nucleic acid molecule, gene or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a host cell, subjected to laboratory manipulation, and reintroduced into a host cell is considered "non-native." Non-native genes include genes endogenous to the host microorganism operably linked to one or more heterologous regulatory sequences that have been inserted into the host genome.

The term, "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, digestion (exonucleolytic or endonucleolytic), ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the term recombinant, engineered, or genetically engineered refers to organisms that have been manipulated by introduction of a heterologous or recombinant nucleic acid sequence into the organism, and includes gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. The heterologous or recombinant nucleic acid molecule can be integrated into the recombinant/genetically engineered organism's genome or in other instances are not integrated into the recombinant/genetically engineered organism's genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term, "expression cassette" as used herein, refers to a nucleic acid construct that encodes a protein or functional RNA (e.g. a tRNA, a short hairpin RNA, one or more microRNAs, a ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

The term, "operably linked" as used herein, denotes a configuration in which a regulatory sequence is placed at an appropriate position relative to a polynucleotide sequence such that the regulatory sequence affects or directs expression of the polynucleotide sequence, for example, to produce a polypeptide and/or functional RNA. Thus, a promoter is in operable linkage with a nucleic acid sequence if it can mediate transcription of the nucleic acid sequence. When introduced into a host cell, an expression cassette can result in transcription and/or translation of an encoded RNA or polypeptide under appropriate conditions. Antisense or sense constructs that are not or cannot be translated are not excluded by this definition.

The term, "exogenous" as used herein in the context of a gene or protein, refers to a gene or protein that is not derived from the host organism species.

The term "transgene" as used herein, refers to an exogenous gene, that is, a gene introduced into a microorganism or a progenitor by human intervention.

The term "heterologous" when used in reference to a polynucleotide, gene, or nucleic acid sequence operably linked to a promoter or other regulatory sequence, refers to a polynucleotide, gene, or nucleic acid sequence, that is not naturally associated with that promoter or regulatory sequence, e.g., the nucleic acid sequence is not associated with the regulatory sequence in the genome of an organism as found in nature. Conversely, when referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

The term, "ortholog" of a gene or protein as used herein, refers to its functional equivalent in another species.

The terms, "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window. The degree of amino acid or nucleic acid sequence identity can be determined by various computer programs for aligning the sequences to be compared based on designated program parameters. For example, sequences can be aligned and compared using the local homology algorithm of Smith & Waterman, *Adv. Appl. Math.* 2:482 (1981), the homology alignment algorithm of Needleman & Wunsch, *J. Mol. Biol.* 48:443 (1970), or the search for similarity method of Pearson & Lipman, *Proc. Nat'l. Acad. Sci. USA* 85:2444 (1988), and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

The BLAST algorithm, described in Altschul et al., *J. Mol. Biol.* 215:403-410 (1990), is publicly available through software provided by the National Center for Biotechnology Information (at the web address www.ncbi.nlm.nih.gov). This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., supra.). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=−4; and a comparison of both strands. The TBLASTN program (using a protein sequence to query nucleotide sequence databases) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

The term, "isolated" biomolecule, such as an isolated protein or nucleic acid as used herein, refers to a biomolecule removed from the context in which the biomolecule exists in nature. An isolated biomolecule can be, in some instances, partially or substantially purified. For example, an isolated nucleic acid molecule can be a nucleic acid sequence that has been excised from the chromosome, genome, or episome into which it is integrated in nature.

The term, "photosynthetic organism" as used herein, is any prokaryotic or eukaryotic organism that can perform photosynthesis. Photosynthetic organisms include higher plants (i.e., vascular plants), bryophytes, algae, and photosynthetic bacteria. The term "algae" includes, but is not limited to, a species of *Bacillariophyceae* (diatoms), *Bolidomonas, Chlorophyceae* (green algae), *Chrysophyceae* (golden algae), *Cyanophyceae* (cyanobacteria), *Eustigmatophyceae* (pico-plankton), *Glaucocystophytes, Pelagophytes, Phaeophyceae* (brown algae), *Prasinophyceae* (pico-plankton), *Raphidophytes, Rhodophyceae* (red algae), *Synurophyceae and Xanthophyceae* (yellow-green algae). The term "microalgae" as used herein refers to microscopic, single-celled algae species including, but not limited to, *Bacillariophyceae, Chlorophyceae*, and *Eustigmatophyceae*. The term "algae" includes microalgae. The term "photosynthetic bacteria" includes, but is not limited to, cyanobacteria, green sulfur bacteria, purple sulfur bacteria, purple non-sulfur bacteria, and green non-sulfur bacteria.

The term, "selectable marker", "selectable marker gene" as used herein, includes any gene that confers a phenotype on a cell in which it is expressed to facilitate the selection of cells that are transfected or transformed with a nucleic acid construct of the invention. The term may also be used to refer to gene products that effectuate said phenotypes. Examples of selectable markers include gene conferring resistance to antibiotics such as amikacin (aphA6), ampicillin ($amp^R$), blasticidin (bls, bsr, bsd), bleomicin or phleomycin (ZEOCIN™) (ble), chloramphenicol (cat), emetine (RBS 14p or cry1-1), erythromycin (ermE), G418 (GENETICIN™) (neo), gentamycin (aac3 or aacC4), hygromycin B (aphIV, hph, hpt), kanamycin (val), methotrexate (DHFR $mtx^R$), penicillin and other β-lactams (β-lactamases), streptomycin or spectinomycin (aadA, spec/strep), and tetracycline (tetA, tetM, tetQ); genes conferring tolerance to herbicides such as aminotriazole, amitrole, andrimid, aryloxyphenoxy propionates, atrazines, bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, urea; including genes encoding enzymes that provde resistance or tolerance to herbicides as acetyl CoA carboxylase (ACCase), acetohydroxy acid synthase (ahas), acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acteyl transferase (pat, bar), phytoene desaturase (ctrI), prenyl transferase, protoporphyrin oxidase, the psbA photosystem II polypeptide (psbA), SMM esterase (SulE) superoxide dismutase (sod); genes that may be used in auxotrophic strains or to confer other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

A "reporter gene" is a gene encoding a protein that is detectable or has an activity that produces a detectable product. A reporter gene can encode a visual marker or enzyme that produces a detectable signal, such as cat, lacZ, uidA, xylE, an alkaline phosphatase gene, an α-amylase gene, an α-galactosidase gene, a β-glucuronidase gene, a β-lactamase gene, a horseradish peroxidase gene, a luciferin/luciferase gene, an R-locus gene, a tyrosinase gene, or a gene encoding a fluorescent protein, including but not limited to a blue, cyan, green, red, or yellow fluorescent protein, a photoconvertible, photoswitchable, or optical highlighter fluorescent protein, or any of variant thereof, including codon-optimized, rapidly folding, monomeric, increased stability, and enhanced fluorescence variants.

The term, "terminator", "terminator sequence" or "transcription terminator" as used herein, refers to a regulatory section of genetic sequence that causes RNA polymerase to cease transcription.

The term, "transgenic" or "recombinant" or "genetically engineered" organism as used herein, refers to an organism that includes at least one exogenous nucleotide sequence, for example, an exogenous gene and/or an exogenous regulatory sequence that was introduced by human intervention. For example, a transgenic microorganism can include an introduced exogenous regulatory sequence operably linked to an endogenous gene of the transgenic microorganism.

The term, "transfection", "transformation", or "transduction" as used herein, refers to the introduction of one or more exogenous nucleic acid sequences or polynucleotides into a host cell or organism by using one or more physical or chemical methods. Biological methods of transformation include transfer of DNA using engineered viruses or microbes (e.g., *Agrobacterium*).

Transcript abundance is measured in terms of reads per kilobase of exon model per million mapped reads ("RPKM") (Mortazavi et al. (2008) *Nature Methods* 5: 621-628). RPKM for a gene is calculated by dividing the gene's total number of exon reads by the product of the number of mapped reads of that gene (in millions) multiplied by the exon length (in kilobases). A gene's total number of exon reads is the number of reads that have been mapped to a region in which an exon is annotated for the gene or across the boundaries of two exons or an intron and an exon for an annotated transcript of the gene. The mapped reads include all the reads uniquely mapped to the region of the gene as well as those of the reads which match in more places that have been allocated to the gene's region. Exon length is calculated as the sum of the lengths of all exons annotated for the gene. Each exon is included only once in this sum, even if it is present in more annotated transcripts for the gene. Partly overlapping exons count for their full length, even though they share the same region.

B. Nucleotide Sequences

Genes were identified and isolated from *Nicotiana gaditana* as sources for promoter and terminator sequences that can find use in the expression of genes, such as but not limited to transgenes, in eukaryotic microorganisms. The method by which these new promoter and terminator sequences were discovered is described more fully in Example 1 herein. Briefly, mRNA was collected and sequenced from *N. gaditana* cultured in nitrogen rich and nitrogen depleted media. Genes were selected whose transcript abundance level was between 150 and 1,500 RPKM, and whose transcript abundance did not change drastically between nitrogen rich and poor culture conditions. The intergenic sequences upstream and downstream of these selected genes were isolated and identified as the promoters and terminators responsible for the regulation of the selected genes' transcription. As a result, SEQ ID NOS:1, 3, 5, 7, and 9 were discovered as comprising promoters that could mediate expression of transgenes in *N. gaditana*, and SEQ ID NOS:2, 4, 6, 8, and 10 were discovered as comprising terminators functional in *N. gaditana*.

Based on the demonstration that these sequences mediate expression of heterologous genes, isolated or recombinant DNA (nucleic acid) molecules are provided herein that correspond to SEQ ID NOS:1-10 and to nucleotide sequences having about 80% identity to at least 100 contiguous nucleotides to any one of SEQ ID NOS:1-10; and further isolated or recombinant nucleic acid molecules having at least 100 contiguous nucleotides to any one of SEQ ID NOS:1-10.

TABLE 1

Regulatory Sequence ID Numbers

| Gene name | Plasmid | Promoter 3'-UTR | Terminator 5'-UTR |
|---|---|---|---|
| Enolase, C-terminal TIM barrel domain | p05133 | SEQ ID NO: 1 | SEQ ID NO: 2 |
| RuBisCo accessory protein AAA type ATPase, cbbX | p05134 | SEQ ID NO: 3 | SEQ ID NO: 4 |
| Eukaryotic initiation factor 4-AIII | p05136 | SEQ ID NO: 5 | SEQ ID NO: 6 |

TABLE 1-continued

| Regulatory Sequence ID Numbers | | | |
|---|---|---|---|
| Gene name | Plasmid | Promoter 3'-UTR | Terminator 5'-UTR |
| Replication factor A protein 3 | p05138 | SEQ ID NO: 7 | SEQ ID NO: 8 |
| Translation initiation factor eIF3 subunit | p05140 | SEQ ID NO: 9 | SEQ ID NO: 10 |

For example, an isolated DNA molecule as provided herein can include: a nucleotide sequence having at least 80% identity to at least 100 contiguous nucleotides of SEQ ID NO:1; a nucleotide sequence having at least 80% identity to at least 100 contiguous nucleotides of SEQ ID NO:3; a nucleotide sequence having at least 80% identity to at least 100 contiguous nucleotides of SEQ ID NO:5; a nucleotide sequence having at least 80% identity to at least 100 contiguous nucleotides of SEQ ID NO:7; or a nucleotide sequence having at least 80% identity to at least 100 contiguous nucleotides of SEQ ID NO:9. In some examples, an isolated DNA molecule as provided herein can include any of: a nucleotide sequence having at least 80% identity to at least 200 contiguous nucleotides of SEQ ID NO:1; a nucleotide sequence having at least 80% identity to at least 200 contiguous nucleotides of SEQ ID NO:3; a nucleotide sequence having at least 80% identity to at least 200 contiguous nucleotides of SEQ ID NO:5; a nucleotide sequence having at least 80% identity to at least 200 contiguous nucleotides of SEQ ID NO:7; or a nucleotide sequence having at least 80% identity to at least 200 contiguous nucleotides of SEQ ID NO:9. In further examples, an isolated DNA molecule as provided herein can include any of: a nucleotide sequence having at least 80% identity to at least 300, at least 400, or at least 500 contiguous nucleotides of SEQ ID NO:1; a nucleotide sequence having at least 80% identity to at least 300, at least 400, or at least 500 contiguous nucleotides of SEQ ID NO:3; a nucleotide sequence having at least 80% identity to at least 300, at least 400, or at least 500 contiguous nucleotides of SEQ ID NO:5; a nucleotide sequence having at least 80% identity to at least 300, at least 400, or at least 500 contiguous nucleotides of SEQ ID NO:7; and a nucleotide sequence having at least 80% identity to at least 300, at least 400, or at least 500 contiguous nucleotides of SEQ ID NO:9. In additional examples, an isolated DNA molecule as provided herein can include a nucleotide sequence having at least 80% identity to SEQ ID NO:1; a nucleotide sequence having at least 80% identity to SEQ ID NO:3; a nucleotide sequence having at least 80% identity to SEQ ID NO:5; a nucleotide sequence having at least 80% identity to SEQ ID NO:7; and a nucleotide sequence having at least 80% identity to SEQ ID NO:9.

For example, an isolated DNA molecule as provided herein can have at least 85% or at least 90% to at least 100, at least 200, at least 300, at least 400, or at least 500 contiguous nucleotides of SEQ ID NO:1, SEQ ID NO:3, SEQ ID NO:5, SEQ ID NO:7, or SEQ ID NO:9, and in some examples, an isolated DNA molecule can have at least 95% sequence identity to at least 100, at least 200, at least 300, at least 400, or at least 500 contiguous nucleotides of SEQ ID NO: 1. Alternatively or in addition, an isolated DNA molecule can have at least 95% sequence identity to at least 100, at least 200, at least 300, at least 400, or at least 500 contiguous nucleotides of SEQ ID NO:3. Further alternatively or additionally, an isolated DNA molecule can have at least 95% sequence identity to at least 100, at least 200, at least 300, at least 400, or at least 500 contiguous nucleotides of SEQ ID NO:5. Further alternatively or additionally, an isolated DNA molecule can have at least 95% sequence identity to at least 100, at least 200, at least 300, at least 400, or at least 500 contiguous nucleotides of SEQ ID NO:7. Further alternatively or additionally, an isolated DNA molecule can have at least 95% sequence identity to at least 100, at least 200, at least 300, at least 400, or at least 500 contiguous nucleotides of SEQ ID NO:9.

In further examples, a nucleic acid molecule can include a nucleotide sequence that can have at least 95%, 96%, 97%, 98%, or 99% percent identity to at least 100 contiguous nucleotides to any one of SEQ ID NOS: 1, 3, 5, 7, or 9.

In particular nonlimiting examples, an isolated DNA molecule can comprise at least 100, at least 200, at least 300, at least 400, or at least 500 contiguous nucleotides of SEQ ID NO:1, at least 100, at least 200, at least 300, at least 400, or at least 500 contiguous nucleotides of SEQ ID NO:3; at least 100, at least 200, at least 300, at least 400, or at least 500 contiguous nucleotides of SEQ ID NO:5; at least 100, at least 200, at least 300, at least 400, or at least 500 contiguous nucleotides of SEQ ID NO:7; or at least 100, at least 200, at least 300, at least 400, or at least 500 contiguous nucleotides of SEQ ID NO:9.

In yet further nonlimiting examples, an isolated DNA molecule can comprise a nucleotide sequence having at least 95% identity to any of SEQ ID NO:1, SEQ ID NO:3, SEQ ID NO:5, SEQ ID NO:7, or SEQ ID NO:9. For example, an isolated DNA molecule can comprise a nucleotide sequence having at least 98% identity to any of SEQ ID NO:1, SEQ ID NO:3, SEQ ID NO:5, SEQ ID NO:7, or SEQ ID NO:9. In further examples, an isolated DNA molecule can comprise any of SEQ ID NO:1, SEQ ID NO:3, SEQ ID NO:5, SEQ ID NO:7, or SEQ ID NO:9.

The isolated DNA molecule can find use, for example, as a sequence that when operably linked to a nucleic acid sequence can affect expression of the nucleic acid sequence, which can comprise, for example, a sequence encoding a polypeptide or functional RNA. For example, the isolated DNA molecule can increase or decrease expression of a nucleic acid sequence (or a portion thereof) to which it is operably linked, or may mediate transcription of the operably-linked nucleic acid sequence (or a portion thereof) as a promoter. Methods for assessing the functionality of nucleotide sequences for promoter activity as well as for enhancing or decreasing the activity of proximal promoters are well-known in the art, and include but are not limited to the in vivo assays disclosed herein using a fluorescent protein gene. Testing of sequence modifications, including deletions and base substitutions of the sequences using reporter constructs such as but not limited to those provided herein are well-known in the art.

Promoters

Also provided herein are promoters comprising a nucleic acid sequence such as any described herein, for example, a nucleic acid sequence having at least 80%, at least 85%, at least 90%, or at least 95% identity to at least 100 contiguous nucleotides of SEQ ID NO:1, SEQ ID NO:3, SEQ ID NO:5, SEQ ID NO:7, or SEQ ID NO:9. For example, a promoter as provided herein may include a nucleotide sequence that has at least 85% or at least 90% sequence identity to at least 100, 200, 300, 400, or 500 contiguous nucleotides of SEQ ID NO:1, at least 85% or at least 90% sequence identity to at least 100, 200, 300, 400, or 500 contiguous nucleotides of SEQ ID NO:3, at least 85% or at least 90% sequence identity to at least 100, 200, 300, 400, or 500 contiguous nucleotides of SEQ ID NO:5, at least 85% or at least 90% sequence identity to at least 100, 200, 300, 400, or 500 contiguous nucleotides of SEQ ID NO:7, or 85% or at least 90% sequence identity to at least at least 100, 200, 300, 400, or 500 contiguous nucleotides of SEQ ID NO:9. In some examples, a promoter can include a sequence that has at least 95% sequence identity to at least 100, 200, 300, 400, or 500 contiguous nucleotides of SEQ ID NO:1, at least 95% sequence identity to at least 100, 200, 300, 400, or 500 contiguous nucleotides of SEQ ID NO:3, at least 95% sequence identity to at least 100, 200, 300, 400, or 500 contiguous nucleotides of SEQ ID NO:5, at least 95% sequence identity to at least 100, 200, 300, 400, or 500 contiguous nucleotides of SEQ ID NO:7, or at least 95% sequence identity to at least 100, 200, 300, 400, or 500 contiguous nucleotides of SEQ ID NO:9. For example, a promoter as provided herein can be selected from the group consisting of an isolated DNA molecule comprising at least 100 contiguous nucleotides of SEQ ID NO:1; an isolated DNA molecule comprising at least 100 contiguous nucleotides of SEQ ID NO:3; a nucleotide sequence comprising at least 100 contiguous nucleotides of SEQ ID NO:5; a nucleotide sequence comprising at least 100 contiguous nucleotides of SEQ ID NO:7; and a nucleotide sequence comprising at least 100 contiguous nucleotides of SEQ ID NO:9.

A promoter provided herein can include a nucleotide sequence having at least 90%, at least 95%, at least 96%, at least 97%, at least 98%, at least 99%, or about 100% identity to at least 250, at least 300, at least 400, at least 500, at least 600, at least 700, at least 800, at least 900, at least 950, or about 1000 contiguous nucleotides of SEQ ID NO:1. For example, a promoter provided herein can have at least 95% sequence identity to SEQ ID NO:1.

Alternatively or additionally, a promoter provided herein can include a nucleotide sequence having at least 90%, at least 95%, at least 96%, at least 97%, at least 98%, at least 99%, or about 100% identity to at least 250, at least 300, at least 400, or at least 500, or about 512 contiguous nucleotides of SEQ ID NO:3. For example, a promoter provided herein can have at least 95% sequence identity to SEQ ID NO:3.

Further alternatively or additionally, a promoter provided herein can include a nucleotide sequence having at least 90%, at least 95%, at least 96%, at least 97%, at least 98%, at least 99%, or about 100% identity to at least 250, at least 300, at least 400, at least 500, at least 600, at least 700, at least 800, or about 823 contiguous nucleotides of SEQ ID NO:5. For example, a promoter provided herein can have at least 95% sequence identity to SEQ ID NO:5.

Further alternatively or additionally, a promoter provided herein can include a nucleotide sequence having at least 90%, at least 95%, at least 96%, at least 97%, at least 98%, at least 99%, or about 100% identity to at least 250, at least 300, at least 400, at least 500, at least 600, at least 700, at least 800, at least 900, at least 950, or about 1000 contiguous nucleotides of SEQ ID NO:7. For example, a promoter provided herein can have at least 95% sequence identity to SEQ ID NO:7.

Further alternatively or additionally, a promoter provided herein can include a nucleotide sequence having at least 90%, at least 95%, at least 96%, at least 97%, at least 98%, at least 99%, or about 100% identity to at least 250, at least 300, at least 400, at least 500, at least 600, at least 700, at least 800, at least 900, at least 950, or about 1000 contiguous nucleotides of SEQ ID NO:9. For example, a promoter provided herein can have at least 95% sequence identity to SEQ ID NO:9.

In various examples of promoters of the present invention a promoter is selected from the group consisting of SEQ ID NO:1, SEQ ID NO:3, SEQ ID NO:5, SEQ ID NO:7, and SEQ ID NO:9.

A promoter as provided herein can be a constitutive promoter, for example the promoter may be active in culture conditions in which one or more nutrients are deficient as well as in culture conditions in which nutrients are sufficient for proliferation and/or growth of the culture. For example, a promoter as provided herein may direct expression of an operably linked nucleic acid sequence under conditions in which a host cell that includes the promoter construct is limited in nitrogen availability (nitrogen depletion) as well as under conditions in which a host cell that includes the promoter construct is not limited in nitrogen availability (nitrogen replete conditions).

Without being bound by theory, promoters allow RNA polymerase to attach to the DNA near a gene in order for transcription to take place. Promoters contain specific DNA sequences that provide transcription factors an initial binding site from which they can recruit RNA polymerase binding. These transcription factors have specific protein motifs that enable them to interact with specific corresponding nucleotide sequences to regulate gene expressions. The minimal portion of the promoter required for proper transcription initiate include: (1) the transcription Start Site ("TSS") and elements directly upstream; (2) an RNA polymerase binding site; and (3) general transcription factor binding sites, e.g. a TATA box (sequence TATAAA). The proximal promoter sequence may be approximately 250 bp upstream of the translational start site of the open reading frame of the gene and may contain, in addition to sequences for binding RNA polymerase, specific transcription factor binding sites. Some promoters also include distal sequence upstream of the gene that may contain additional regulatory elements, often with a weaker influence than the proximal promoter. Eukaryotic transcriptional complexes can bend the DNA back on itself, thus allowing for potential placement of additional regulatory sequences as far as several kilobases from the TSS. Many eukaryotic promoters contain a TATA box. The TATA box binds the TATA binding protein, which assists in the formation of the RNA polymerase transcriptional complex. TATA boxes usually lie within approximately 50 bp of the TSS. A promoter may be constitutive or expressed conditionally. Some promoters are inducible, and may activate or increase transcription in response to an inducing agent. In contrast, the rate of transcription of a gene under control of a constitutive promoter is not dependent on an inducing agent. A constitutive promoter can be made a conditional or inducible promoter by the addition of sequences that confer responsiveness to particular conditions or to an inducing agent. Thus, promoters provided herein may be constitutive or may be inducible or conditional. Further, promoters or portions of promoters may be combined in series to achieve a stronger level of expression or a more complex pattern of regulation.

In various examples, a promoter as provided herein, such as but not limited to a promoter that comprises a nucleotide sequence having at least 80%, at least 85%, at least 90%, at least 95%, at least 96%, at least 97%, at least 98%, at least 99%, or about 100% identity to at least 100, at least 200, at least 300, at least 400, or at least 500 contiguous nucleotides of SEQ ID NO:1, SEQ ID NO:3, SEQ ID NO:5, SEQ ID NO:7, or SEQ ID NO:9, can mediate transcription of an operably linked nucleic acid sequence in a eukaryotic algal cell, such as, for example, a *Nannochloropsis* cell. In some instances, a promoter as provided herein can mediate transcription of an operably linked nucleic acid sequence in a eukaryotic cell, such as but not limited to a eukaryotic algal cell, during culturing of the cell under conditions of nitrogen depletion as well as during culturing of the cell under nitrogen replete conditions. For example, a promoter as described herein can preferably mediate transcription of an operably linked nucleic acid sequence in *Nannochloropsis* cells cultured under conditions of nitrogen depletion or cultured under nitrogen replete conditions.

Additionally, as contemplated herein, a promoter or promoter region can include variants of the promoters disclosed herein derived by deleting sequences, duplicating sequences, or adding sequences from other promoters or as designed, for example, by bioinformatics, or by subjecting the promoter to random or site-directed mutagenesis, etc.

Any of the nucleic acid molecules described herein may comprise nucleic acid sequences comprising promoters. For example, promoters of the present invention can include nucleic acid sequences having at least 80%, at least 85%, at least 90%, at least 95%, or between 95% and 100% identity to the sequences between about 0 bp, 20 bp, 50 bp, 100 bp, 200 bp or 300 bp to about 500 bp, 600 bp, 700 bp, 800 bp, 900 bp, or 1 kb upstream of the trinucleotide ATG sequence at the start site of a protein coding region of a native *Nannochloropsis* gene, such as, for example, an enolase (C-terminal TIM barrel domain-containing) gene, a RuBisCo accessory protein AAA type ATPase (cbbX) gene, a eukaryotic initiation factor 4-AIII gene, a replication factor A protein 3 gene, and a translation initiation factor eIF3 subunit gene.

The activity or strength of a promoter may be measured in terms of the amounts of RNA it produces, or the amount of protein accumulation in a cell or tissue, which can optionally be measured by an activity of the expressed protein, e.g., fluorescence, luminescence, acyltransferase activity, etc., relative to a promoter whose transcriptional activity has been previously assessed, relative to a promoter-less construct, or relative to non-transformed cells. For example, the activity or strength of a promoter may further be measured in terms of the amount of mRNA accumulated that corresponds to a nucleic acid sequence it is operably linked to in a cell, relative to the total amount of mRNA or protein produced by the cell. The promoter preferably expresses an operably linked nucleic acid sequence at a level greater than 0.01%; preferably in a range of about 0.5% to about 20% (w/w) of the total cellular RNA. The activity can also be measured by quantifying fluorescence, luminescence, or absorbance of the cells or a product made by the cells or an extract thereof, depending on the activity of a reporter protein that may be expressed from the promoter. The activity or strength of a promoter may be expressed relative to a well-characterized promoter (for which transcriptional activity was previously assessed). For example, a less-characterized promoter may be operably linked to a reporter sequence (e.g., a fluorescent protein) and introduced into a specific cell type. A well-characterized promoter is similarly prepared and introduced into the same cellular context. Transcriptional activity of the unknown promoter is determined by comparing the amount of reporter expression, relative to the well characterized promoter.

A promoter described herein can have promoter activity in a eukaryotic cell, preferably in an algal cell or heterokont cell. In a particular examples, a promoter as provided herein is active in an algal or heterokont cell in nutrient replete and nutrient-depleted culture conditions. An algal promoter as provided herein can be used as a 5' regulatory element for modulating expression of an operably linked gene or genes in algal species as well as other organisms, including fungi, heterokonts, and plants.

Using promoter assay methods, such as but not limited to the method described in Example 1, the disclosed promoter sequences can be further modified, e.g. truncated or mutated, and screened to refine the active promoter regions.

Terminators

In another embodiment of the present invention terminators are provided in which the terminators comprise a nucleotide sequence having at least 80%, at least 85%, at least 90%, at least 95%, at least 96%, at least 97%, at least 98%, at least 99%, or about 100% identity to at least 100 or at least 150 contiguous nucleotides of SEQ ID NO:2, SEQ ID NO:4, SEQ ID NO:6, SEQ ID NO:8, or SEQ ID NO:10.

For example, a terminator can have at least 80%, at least 85%, at least 90%, at least 95%, at least 96%, at least 97%, at least 98%, at least 99%, or about 100% identity to at least 200, at least 300, at least 400, at least 500, at least 600, at least 700, at least 800, at least 900, at least 950, or about 998 contiguous nucleotides of SEQ ID NO:2.

Alternatively or in addition, a terminator can have at least 80%, at least 85%, at least 90%, at least 95%, at least 96%, at least 97%, at least 98%, at least 99%, or about 100% identity to at least 200, at least 300, at least 400, at least 450, or about 474 contiguous nucleotides of SEQ ID NO:4.

Alternatively or in addition, a terminator can have at least 80%, at least 85%, at least 90%, at least 95%, at least 96%, at least 97%, at least 98%, at least 99%, or about 100% identity to about 175 contiguous nucleotides of SEQ ID NO:6.

Alternatively or in addition, a terminator can have at least 80%, at least 85%, at least 90%, at least 95%, at least 96%, at least 97%, at least 98%, at least 99%, or about 100% identity to at least 200, at least 300, or about 337 contiguous nucleotides of SEQ ID NO:8.

Alternatively or in addition, a terminator can have at least 80%, at least 85%, at least 90%, at least 95%, at least 96%, at least 97%, at least 98%, at least 99%, or about 100% identity to at least 200, at least 300, or about 306 contiguous nucleotides of SEQ ID NO:10.

Terminators are genetic sequences that mark the end of a gene for transcription. Without being bound by theory, the terminators of the present invention may improve expression improve expression of the nucleic acid sequence (amount of encoded RNA or protein produced), and may mediate polyadenylation or enhance RNA transcript stability. Most terminator sequences in eukaryotes consist of at least two DNA sequences: (1) a binding site for terminator proteins and (2) an upstream element located among the last twelve nucleotides of the transcript. The protein binding sites are usually orientation-sensitive and essential to termination. Termination usually occurs between twelve and twenty nucleotides upstream of the binding site. The upstream element's functionality usually depends more on its overall base composition (T-rich) than on the specific sequence (Reeder & Lang (1997) *Trends Biochem Sci.* 22:473-477, herein incorporated by reference in its entirety).

C. Expression Cassettes

Expression cassettes are also provided in the present invention, in which the expression cassettes comprise one or more regulatory elements as described herein to drive the expression of transgenes. These cassettes comprise isolated nucleic acid molecules that include any one of the promoter sequences described herein or any combination thereof, operably linked to a gene of interest with the gene of interest positioned downstream of the promoter sequence, and optionally with any one of the terminator sequences described herein or any combination thereof operably linked downstream of the transgene. The basic techniques for operably linking two or more sequences of DNA together are familiar to the skilled worker, and such methods have been described in a number of texts for standard molecular biological manipulation (see, e.g., "*Molecular Cloning: A Laboratory Manual,*" 2$^{nd}$ ed. Cold Spring Harbor Laboratory Press, Cold Spring Harbor, N.Y.; Gibson et al. (2009) *Nature Methods* 6:343-345).

The promoters of the invention can be used with any heterologous genes. A heterologous gene according to the invention may encode a protein or polypeptide. Alternatively, the heterologous gene can encode a functional RNA, such as a tRNA, rRNA, small nucleolar RNA (snoRNA), ribozyme, antisense RNA (asRNA), micro RNA (miRNA), short hairpin RNA (shRNA), silencing RNA (siRNA), or piwi-interacting RNA (piRNA). Any known or later-discovered heterologous gene which encodes a desired product can be operably linked to a promoter sequence of the invention using known methods. Non-limiting examples of known heterologous genes suitable for use with the promoters of the invention include genes encoding proteins associated with lipid biosynthesis; lipases; proteins associated with carbohydrate metabolism; transporter polypeptides; proteins conferring resistance to an antibiotic, herbicide, or toxin; reporter proteins (e.g., fluorescent proteins or enzymes that produce detectable products) polypeptides of the Calvin-Benson cycle; polypeptides that participate in photosynthesis (such as but not limited to, photosynthetic reaction center polypeptides, light-harvesting chlorophyll-binding proteins, oxygen-evolving complex polypeptides, cytochromes, ferredoxins, etc.); dehdrogenases, such as NADPH-forming dehydrogenases; transcription factors; proteins involved in cell signaling (e.g., G proteins or kinases); or functional RNAs.

TABLE 2

| Expression Cassettes | |
|---|---|
| Promoter/Terminator pair | Sequence |
| Translation initiation factor eIF3 subunit | SEQ ID NO:12 |
| Enolase, C-terminal TIM barrel domain | SEQ ID NO:13 |
| RuBisCo accessory protein AAA type ATPase, cbbX | SEQ ID NO:14 |
| Eukaryotic initiation factor 4-AIII | SEQ ID NO:15 |
| Replication factor A protein 3 | SEQ ID NO:16 |

For example, an expression cassette can comprise a promoter as described herein (for example, a promoter comprising a nucleotide sequence having at least 80% identity to at least 100 contiguous nucleotides SEQ ID NO:1, 3, 5, 7, or 9) operably linked to a gene encoding a polypeptide, where the polypeptide can be any polypeptide of interest, and in illustrative and nonlimiting examples, can be a protein associated with lipid biosynthesis, an acetyl-CoA carboxylase, a malonyl type 1 fatty acid synthase, a type 2 fatty acid synthase subunit, a beta ketoacyl-ACP synthase, a malonyl-CoA-malonyl-ACP acyltransferase, an acyl-ACP thioesterase, an acyl-CoA thioesterase, a 4-hydroxybenzoyl thioesterase, an alcohol forming acyl reductase, a wax synthase, an aldehyde decarbonylase, a fatty acid decarboxylase, a lipase, a glyceraldehyde 3 phosphate dehydrogenase, an acyl-CoA synthetase, a phospholipid diacylglycerol acyltransferase, a glycerol 3 phosphate acyltransferase, a lysophosphatidic acid acyltransferase, a phosphatidic acid phosphatase, a diacyl glycerol acyltransferase, a polypeptide that participates in photosynthesis, a chlorophyll-binding light harvesting polypeptide, a photosynthetic reaction center polypeptide, an oxygen-evolving complex polypeptide, a cytochrome, a ferredoxin, a protein associated with carbon fixation, a ribulose bisphoshate carboxylase subunit, a carbonic anhydrase, a transporter protein, an ABC transporter, a FatB transporter, a dehydrogenase, an aldehyde dehydrogenase, a 2-hydroxyacid dehydrogenase, an isocitrate dehydrogenase, 6 phosphogluconate dehydrogenase, glucose 6 phosphate dehydrogenase, a transcription factor, a kinase, or a G protein.

In further examples, an expression cassette can comprise a promoter as described herein (for example, a promoter comprising a nucleotide sequence having at least 80% identity to at least 100 contiguous nucleotides SEQ ID NO:1, 3, 5, 7, or 9) operably linked to a gene encoding a functional RNA, optionally wherein the functional RNA is an antisense RNA, a small hairpin RNA, a microRNA, an siRNA, an snoRNA, a piRNA, or a ribozyme.

D. Vectors

The present invention also provides vectors that can comprise the regulatory elements and/or expression cassettes described herein. The vectors comprise the expression cassettes described herein and further include at least one origin of replication ("ORI") sequence for replication in a cell. The vectors may further optionally comprise one or more selectable markers under the control of one or more eukaryotic promoters, one or more selectable markers under the control of one or more prokaryotic promoters, and/or one or more sequences that mediate recombination of an exogenous nucleic acid sequence into the target cell's genome.

An ORI is the sequence in a DNA molecule at which replication begins. The ORI serves as a base of assembly for the pre-replication complex. Depending on the ORI, such replication can proceed unidirectionally or bidirectionally. An expression vector as provided herein can include an ORI for replication of the expression vector in a cloning host, such as *E. coli* or *Saccharomyces*, and/or can include an ORI for replication of the expression vector in a target cell, which can be, for example, an algal or heterokont cell. The structural biology of ORIs is widely conserved among prokaryotes, eukaryotes, and viruses. Most ORIs possess simple tri-, tetra-, or higher nucleotide repetition patterns. Most are AT-rich and contain inverted repeats. Those skilled in the art will be familiar with the more common ORIs, such as P15A and the pUC ORI.

A vector may also carry a selectable marker. By way of example, a vector that includes an expression cassette may include, as a selectable marker, a gene conferring resistance to a poison, such as an antibiotic, a herbicide, or some other toxin, so that transformants can be selected by exposing the cells to the poison and selecting those cells which survive the encounter. Non-limiting examples of selectable markers include: Examples of selectable markers include gene conferring resistance to antibiotics such as amikacin (aphA6), ampicillin (amp$^R$), blasticidin (bls, bsr, bsd), bleomicin or phleomycin (ZEOCIN™) (ble), chloramphenicol (cat), emetine (RBS 14p or cry1-1), erythromycin (ermE), G418 (GENETICIN™) (neo), gentamycin (aac3 or aacC4), hygromycin B (aphIV, hph, hpt), kanamycin (ntpII), methotrexate (DHFR mtx$^R$), penicillin and other β-lactams (β-lactamases), streptomycin or spectinomycin (aadA, spec/strep), and tetracycline (tetA, tetM, tetQ); genes conferring tolerance to herbicides such as aminotriazole, amitrole, andrimid, aryloxyphenoxy propionates, atrazines (psbA), bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, or urea compounds; including genes encoding enzymes that provde resistance or tolerance to herbicides as acetyl CoA carboxylase (ACCase), acetohydroxy acid synthase (ahas), acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acteyl transferase (pat, bar), phytoene desaturase (crtI), prenyl transferase, protoporphyrin oxidase, psbA of photosystem II (psbA), SMM esterase (SulE) superoxide dismutase (sod); genes that may be used in auxotrophic strains or to confer autotrophic growth or other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene. The selectable marker gene can be operably linked to a promoter as provided herein.

The selectable marker may be under the control of a promoter including but not limited to a promoter as provided herein. The promoter regulating expression of the selectable marker may be conditional or inducible but is preferably constitutive, and can be, for example, any promoter disclosed herein or another promoter. Alternatively, the selectable marker may be placed under the control of the expression cassette promoter. If a selectable marker is placed under the control of the expression cassette promoter, the selectable marker and the expression cassette may be operably linked with an internal ribosome entry site ("IRES") element between the expression cassette and the selectable marker (Komar & Hatzoglou (2011) *Cell Cycle* 10:229-240 and Hellen & Sarnow (2001) Genes & Dev. 15:1593-1612, incorporated by reference in their entireties) or a "2A" sequence (Kim et al. (2011) *PLoS One* 6(4):e18556, incorporated by reference in its entirety).

Further provided herein is a vector for transformation of a eukaryotic cell, such as but not limited to a eukaryotic microalgal cell or a heterokont cell, in which the vector includes a selectable marker gene operably linked to a promoter as provided herein, for example, a promoter that includes a nucleotide sequence having at least 80%, at least 85%, at least 90%, at least 95%, at least 96%, at least 97%, at least 98%, at least 99%, or about 100% identity to at least 100, at least 200, at least 300, at least 400, at least 500, at least 600, at least 700, or at least 800 contiguous nucleotides of SEQ ID NO:1; SEQ ID NO:3, SEQ ID NO:5, SEQ ID NO:7, or SEQ ID NO:9, or a promoter that comprises SEQ ID NO:1; SEQ ID NO:3, SEQ ID NO:5, SEQ ID NO:7, or SEQ ID NO:9. The transformation can further include one or more additional genes or constructs for transfer into the host cell, such as a gene encoding a polypeptide such as but not limited to any disclosed hereinabove or a construct encoding a functional RNA, where the gene encoding a polypeptide or functional RNA can optionally be operably linked to a promoter as described herein, or can optionally be operably linked to another promoter.

In an alternative transformation strategy, a selectable marker operably linked to a promoter such as a promoter described herein can be provided on a separate construct, where both the gene-of-interest construct and the selectable marker construct are used together in transformation protocols. Selected transformants are then analyzed for co-transformation of the construct that includes the gene-of-interest (see, e.g., Kindle (1990) *Proc. Natl. Acad. Sci. USA* 87:1228-1232).

If a vector as provided herein that includes an expression cassette lacks a selectable marker gene, transformants may be selected by routine methods familiar to those skilled in the art, such as, by way of a non-limiting example, extracting nucleic acid from the putative transformants and screening by PCR. Alternatively or in addition, transformants may be screened by detecting expression of a reporter gene, such as but not limited to a chloramphenicol acyltransferase gene (cat) lacZ, uidA, xylE, an alkaline phosphatase gene, an α-amylase gene, an α-galactosidase gene, a β-lactamase gene, a β-glucuronidase gene, a horseradish peroxidase gene, a luciferin/luciferase gene, an R-locus gene, a tyrosinase gene, or a gene encoding a fluorescent protein, such as any of the green, yellow, red, blue, cyan, photoconvertable, or photoswitchable fluorescent proteins or any of their variants, including codon-optimized, rapidly folding, monomeric, increased stability, and enhanced fluorescence variants. A reporter gene used in a vector may optionally be regulated by a promoter as provided herein. A transformation vector may include a gene encoding a reporter, such as, for example, a fluorescent protein, operably linked to a promoter as provided herein.

In some embodiments, the vector is designed for integration of one or more genes (such as the expression cassette) into the host genome. For example, the expression vectors may include *Agrobacterium* flanking sequences designed for integrating transgenes into the genome of a target plant cell. In other embodiments, vectors can be targeted for integration into a plant or algal chromosome by including flanking sequences that enable homologous recombination into the chromosome or targeted for integration into endogenous host plasmids by including flanking sequences that enable homologous recombination into the endogenous plasmids. In some cases in which it may be advantageous to transform the chloroplast of a higher plant or alga, the expression vectors can be designed to have regions of sequences flanking the transgene that are homologous to chloroplast sequences to promote homologous recombination and integration of the sequence of interest. Further, a transformation vector can include sequences for site-specific recombination such as but not limited to lox sites that are acted on by the cre recombinase.

In addition to the promoters provided herein, one skilled in the art would know various promoters, introns, enhancers, transit peptides, targeting signal sequences, 5' and 3' untranslated regions (UTRs), IRES, 2A sequences, and terminator sequences, as well as other molecules involved in the regulation of gene expression that are useful in the design of effective expression vectors. In some embodiments, the expression vector will contain one or more enhancer elements. Enhancers are short regions of DNA that can bind trans-acting factors to enhance transcription levels. Although enhancers usually act in cis, an enhancer need not be particularly close to its target gene, and may sometimes not be located on the same chromosome. Enhancers can sometimes be located in introns.

In some examples, a gene or genes encoding enzymes that participate in the synthesis of a fatty acid product (e.g., a fatty acid, a fatty caid derivative, or a glycerolipid) is cloned into the vector as an expression cassette that includes a promoter as disclosed herein. The expression cassette may optionally include a transit peptide-encoding sequence for directing the expressed enzyme to the chloroplast or endoplasmic reticulum of transformed eukaryotic cells, an intron sequence, a sequence having a poly-adenylation signal, etc.

In a further embodiment, a vector is provided comprising an expression cassette as described herein, wherein the vector further comprises one or more of: a selectable marker gene, an origin of replication, and one or more sequences for promoting integration of the expression cassette into the host genome.

In a further embodiment, a vector is provided comprising an isolated or recombinant nucleic acid molecule as described herein, wherein the isolated nucleic acid molecule is operably linked to a nucleic acid sequence encoding a selectable marker or a reporter protein, such as, for example, any described herein. In a particular embodiment, the vector further comprises one or more of: an origin of replication, one or more sequences for promoting integration of the expression cassette into the host genome, a sequence as reported herein that comprises a terminator, or an additional gene, wherein the additional gene encodes an antisense RNA, a microRNA, an shRNA, a ribozyme, structural protein, an enzyme, a transcription factor, or a transporter.

E. Transformation Methods

The present invention provides transformation methods in which a eukaryotic cell is transformed with an expression vector as described herein. The methods comprise introducing an expression vector as provided herein that includes a promoter as disclosed herein operably linked to a selectable marker gene into a host cell and then selecting for a transformant. The expression vector may be introduced by many methods familiar to those skilled in the art including, as non-limiting examples: natural DNA uptake (Chung et al. (1998) *FEMS Microbiol. Lett.* 164:353-361); conjugation (Wolk et al. (1984) *Proc. Natl. Acad. Sci. USA* 81, 1561-1565); transduction; glass bead transformation (Kindle et al. (1989) *J. Cell Biol.* 109:2589-601); silicon carbide whisker transformation (Dunahay et al. (1997) *Methods Mol. Biol.* (1997) 62:503-9); biolistics (Dawson et al. (1997) *Curr. Microbiol.* 35:356-62); electroporation (Kjaerulff et al. (1994) *Photosynth. Res.* 41:277-283); laser-mediated transformation; or incubation with DNA in the presence of or after pre-treatment with any of poly(amidoamine) dendrimers (Pasupathy et al. (2008) Biotechnol. J. 3:1078-82), polyethylene glycol (Ohnuma et al. (2008) *Plant Cell Physiol.* 49:117-120), cationic lipids (Muradawa et al. (2008) *J. Biosci. Bioeng.* 105:77-80), dextran, calcium phosphate, or calcium chloride (Mendez-Alvarez et al. (1994) *J. Bacteriol.* 176:7395-7397), optionally after treatment of the cells with cell wall-degrading enzymes (Perrone et al. (1998) *Mol. Biol. Cell* 9:3351-3365). *Agrobacterium*-mediated transformation can also be performed on algal cells, for example after removing or wounding the algal cell wall (e.g., WO 2000/62601). Biolistic methods have been shown to be successful for transformation of the chloroplasts of plant and eukaryotic algal species (see, e.g., WO 2007/133558, incorporated by reference in its entirety).

The eukaryotic cell transformed can be, for example, a fungal, heterokont, algal, or plant cell. For example, the eukaryotic cell transformed using an expression vector as provided herein can be an algal cell, such as a species of *Bacillariophyceae* (diatoms), *Bolidomonas, Chlorophyceae* (green algae), *Chrysophyceae* (golden algae), *Cyanophyceae* (cyanobacteria), *Eustigmatophyceae* (pico-plankton), *Glaucocystophytes, Pelagophyceae, Bolidophyceae, Prasinophyceae* (pico-plankton), *Raphidophyceae, Rhodophyceae* (red algae), *Synurophyceae* and *Xanthophyceae* (yellow-green algae), and can be a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria*, or *Volvox*. For example, the eukaryotic cell transformed using the methods provided herein can optionally be a species of *Nannochloropsis*, such as *Nannochloropsis gaditana, Nannochloropsis granulata, Nannochloropsis limnetica, Nannochloropsis maritima, Nannochloropsis oceanica, Nannochloropsis oculata*, or *Nannochloropsis salina*.

In further examples, the eukaryotic cell can be a heterokont cell, optionally, a species the order Chytridiomycota or Labyrinthulales, preferably a species of *Thraustochytrid, Thraustochytrium, Labrynthula, Labyrinthuloides, Japonochytrium*, or *Schizochytrium*.

In some examples, a *Nannochloropsis* cell is transformed by electroporation or particle bombardment. The expression vector used to transform the host cell may encode, for a selectable marker, a green fluorescent protein such as GFP, a polypeptide, or a functional RNA.

F. Culture

Eukaryotic host cells, such as any of the cells disclosed hereinabove transformed with the expression vectors are also provided herein. Transformed algal cell cultures can be diluted, plated on agar, and allowed to grow until isolated colonies can be selected for further propagation as clonal strains.

Therefore, in one embodiment a eukaryotic cell is provided comprising an isolated or recombinant nucleic acid molecule as described herein or an expression cassette as described herein, or a vector as described herein.

Algae can be cultured phototrophically, in the absence of a fixed carbon source, or mixotrophically, where the cultures are supplied with light for at least part of the day, and also supplied with a reduced carbon source, such as a sugar (e.g., glucose, fructose, galactose, mannose, rhamnose, arabinose, xylose, lactose, sucrose, maltose), an organic acid (e.g., acetate, citrate, succinate), or glycerol. The photosynthetic organism in some embodiments is cultured mixotrophically, in which the organism is grown in the presence of light for at least a part of the day, and also provided with one or more sources of reduced carbon. A photosynthetic organism can be grown mixotrophically for a period of time, followed by a period of phototrophic growth, or vice versa.

Media for phototrophic or mixotrophic growth of algae are known in the art, and media can be optimized to enhance growth or production of fatty acid products for a particular species. Artificial light sources can be used as the sole light source or to enhance or extend natural light.

Growth of algae can be in open areas, such as, for example, ponds, canals, channels, raceways, or tanks, or can be in bioreactors. Bioreactors are preferred for mixotrophic growth, and can also be used for phototrophic growth. The bioreactors can be of any sizes and form, and can include inlets for providing nutrients, additives, or gases, such as but not limited to air or $CO_2$. A bioreactor preferably also has an outlet for sampling of the culture. A bioreactor can be configured such that the algal culture is mixed during the growth period, for example, by stirring, rocking, shaking, inverting, bubbling of gases through the culture, etc. Outdoor ponds, raceways, tanks, canals, etc. can also be designed for mixing of cultures through, for example, paddles, pumps, hoses or jets for circulation of the culture media, or tubes, hoses or inlets for supplying air or $CO_2$ to the culture.

G. Research Methods

Research methods for detecting promoter activity in a heterokont or algal cell are also provided, comprising (1) transforming an algal cell culture with a vector that includes (a) a fluorescent protein-encoding sequence operably linked to a putative promoter sequence and (b) a selectable marker, to produce a transformation culture; (2) plating the transformation culture on agar containing a selection agent and allowing transformed heterokont or algal colonies to grow on agar; and 3) measuring fluorescent protein signal(s) of the colonies to identify at least one colony that includes a promoter sequence upstream of the fluorescent protein gene.

In particular examples, a putative promoter sequence to be tested can be derived from the nuclear genome of an algal species or heterokont species. The putative promoter sequence can be a sequence comprising a promoter that has been mutated, truncated, internally deleted, or modified, for example, by the substitution or addition of one ore more nucleotides. The methods can include transforming an algal or heterokont culture with a library of vectors containing different algla or heterokont putative promoters and/or different mutated versions of a putative or known promoter.

The methods can also include cloning one or more putative promoter sequences upstream of a gene encoding a fluorescent protein in a vector that also includes a selectable marker gene prior to transforming an algal or heterokont cell culture.

The methods can also include isolating DNA from a transformant cultured from a fluorescent colony to determine the sequence of the promoter.

In further examples, the cells can be optionally allowed an incubation period after the transformation but before the plating, with or without selective agents, during which they can produce a fluorescent protein. The incubated cells can then be examined by flow cytometry prior to plating. In some examples, the transformation culture is analyzed or sorted by flow cytometry before selecting a transformation culture on agar plates. For example, a sub-population may be used for plating, based on a fluorescence threshold used for flow cytometry-based cell sorting.

Where the promoter whose activity is being tested is thought to be nitrogen-sensitive, the plates on which the transformants are grown can be enriched-in or depleted of nitrogen. For example, the transformants may be selected on nitrogen replete media to identify promoter sequences that mediate transcription under nitrogen replete conditions.

The methods described herein can be used in any algal species, such as any disclosed herein, or can be used in a heterokont species as disclosed herein. For example, the methods can be used to determine promoters active in a *Nannochloropsis* species. In illustrative examples, GFP is used as the reporter protein for detecting promoter activity, but any other fluorescent proteins can also be used. Reporter genes operably linked to a putative promoter sequence can also be used to assess the strength of a promoter by comparing the strength of the signal from colonies on agar plates.

H. Further Embodiments

Embodiment 1

An isolated or recombinant nucleic acid molecule comprising a nucleotide sequence having at least 80%, at least 85%, at least 90%, at least 95%, at least 96%, at least 97%, at least 98%, at least 99%, or 100% identity to at least 100, at least 200, at least 300, at least 400, or at least 500, contiguous nucleotides of SEQ ID NO:1, SEQ ID NO:3, SEQ ID NO:5, SEQ ID NO:7, or SEQ ID NO:9.

Embodiment 2

The isolated or recombinant nucleic acid molecule of Embodiment 1, wherein at least one of the following are satisfied:

the nucleic acid molecule has promoter activity in a eukaryotic cell, preferably an algal cell or heterokont cell;

the isolated nucleic acid molecule has at least 80%, at least 85%, at least 90%, at least 95%, at least 96%, at least 97%, at least 98%, at least 99%, or about 100% identity to at least 600, at least 700, at least 800, at least 900, at least 950, or about 1000 contiguous nucleotides of SEQ ID NO:1;

the isolated nucleic acid molecule has at least 80%, at least 85%, at least 90%, at least 95%, at least 96%, at least 97%, at least 98%, at least 99%, or about 100% identity to about 512 contiguous nucleotides of SEQ ID NO:3;

the isolated nucleic acid molecule has at least 80%, at least 85%, at least 90%, at least 95%, at least 96%, at least 97%, at least 98%, at least 99%, or about 100% identity to at least 600, at least 700, at least 800, or about 823 contiguous nucleotides of SEQ ID NO:5;

the isolated nucleic acid molecule has at least 80%, at least 85%, at least 90%, at least 95%, at least 96%, at least 97%, at least 98%, at least 99%, or about 100% identity to at least 600, at least 700, at least 800, at least 900, at least 950, or about 1000 contiguous nucleotides of SEQ ID NO:7;

the isolated nucleic acid molecule has at least 80%, at least 85%, at least 90%, at least 95%, at least 96%, at least 97%, at least 98%, at least 99%, or about 100% identity to at least 600, at least 700, at least 800, at least 900, at least 950, or about 1000 contiguous nucleotides of SEQ ID NO:9;

the isolated nucleic acid molecule comprises a constitutive promoter; and the isolated nucleic acid is molecule comprises a promoter active in a eukaryotic cell in nutrient replete and nutrient deficient culture conditions.

Embodiment 3

An isolated or recombinant nucleic acid molecule comprising a nucleotide sequence having at least 80%, at least 85%, at least 90%, at least 95%, at least 96%, at least 97%, at least 98%, at least 99%, or about 100% identity to at least 100, or at least 150 contiguous nucleotides of SEQ ID NO:2, SEQ ID NO:4, SEQ ID NO:6, SEQ ID NO:8, or SEQ ID NO:10, optionally wherein at least one of the following are satisfied:

the isolated nucleic acid molecule has at least 80%, at least 85%, at least 90%, at least 95%, at least 96%, at least 97%, at least 98%, at least 99%, or about 100% identity to at least 200, at least 300, at least 400, at least 500, at least 600, at least 700, at least 800, at least 900, at least 950, or about 998 contiguous nucleotides of SEQ ID NO:2;

the isolated nucleic acid molecule has at least 80%, at least 85%, at least 90%, at least 95%, at least 96%, at least 97%, at least 98%, at least 99%, or about 100% identity to at least 200, at least 300, at least 400, at least 450, or about 474 contiguous nucleotides of SEQ ID NO:4;

the isolated nucleic acid molecule has at least 80%, at least 85%, at least 90%, at least 95%, at least 96%, at least 97%, at least 98%, at least 99%, or about 100% identity to about 175 contiguous nucleotides of SEQ ID NO:6;

the isolated nucleic acid molecule has at least 80%, at least 85%, at least 90%, at least 95%, at least 96%, at least 97%, at least 98%, at least 99%, or about 100% identity to at least 200, at least 300, or about 337 contiguous nucleotides of SEQ ID NO:8;

the isolated nucleic acid molecule has at least 80%, at least 85%, at least 90%, at least 95%, at least 96%, at least 97%, at least 98%, at least 99%, or about 100% identity to at least 200, at least 300, or about 306 contiguous nucleotides of SEQ ID NO:10;

wherein the isolated or recombinant nucleic acid molecule preferably comprises a terminator sequence.

Embodiment 4

An expression cassette comprising the isolated nucleic acid molecule of Embodiment 1 or Embodiment 2, wherein:

a) the isolated nucleic acid molecule is operably linked to a gene encoding a polypeptide, optionally wherein the polypeptide is:

a protein associated with lipid biosynthesis, an acetyl-CoA carboxylase, a malonyl type 1 fatty acid synthase, a type 2 fatty acid synthase subunit, a beta ketoacyl-ACP synthase, a malonyl-CoA-malonyl-ACP acyltransferase, an acyl-ACP thioesterase, an acyl-CoA thioesterase, a 4-hydroxybenzoyl thioesterase, an alcohol forming acyl reductase, a wax synthase, an aldehyde decarbonylase, a fatty acid decarboxylase, a lipase, a glyceraldehyde 3 phosphate dehydrogenase, an acyl-CoA synthetase, a phospholipid diacylglycerol acyltransferase, a glycerol 3 phosphate acyltransferase, a lysophosphatidic acid acyltransferase, a phosphatidic acid phosphatase, a diacyl glycerol acyltransferase, a polypeptide that participates in photosynthesis, a chlorophyll binding light harvesting polypeptide, a photosynthetic reaction center polypeptide, an oxygen-evolving complex polypeptide, a cytochrome, a ferredoxin, a protein associated with carbon fixation, a ribulose bisphoshate carboxylase subunit, a carbonic anhydrase, a transporter protein, an ABC transporter, a FatB transporter, a dehydrogenase, an aldehyde dehydrogenase, a 2-hydroxyacid dehydrogenase, an isocitrate dehydrogenase, 6 phosphogluconate dehydrogenase, glucose 6 phosphate dehydrogenase; a transcription factor, a kinase, or a G protein; or (b) the isolated nucleic acid molecule is operably linked to a gene encoding a functional RNA, optionally wherein the functional RNA is an antisense RNA, a small hairpin RNA, a microRNA, an antisense RNA, a siRNA, a piRNA, or a ribozyme;

wherein the expression cassette optionally further comprises a nucleotide sequence according to Embodiment 3.

Embodiment 5

An expression vector comprising the expression cassette of embodiment 4, wherein the expression vector further comprises one or more of:

a selectable marker gene, an origin of replication, and one or more sequences for promoting integration of the expression cassette into the host genome.

Embodiment 6

A vector comprising the isolated nucleic acid molecule of Embodiment 1 or Embodiment 2, wherein the isolated nucleic acid molecule is operably linked to a nucleic acid sequence encoding a selectable marker or a reporter protein, optionally wherein the selectable marker protein is selected from the group consisting of: amikacin (aphA6), ampicillin ($amp^R$), blasticidin (bls, bsr, bsd), bleomicin or phleomycin (ZEOCIN™) (ble), chloramphenicol (cat), emetine (RBS 14p or cry1-1), erythromycin (ermE), G418 (GENETICIN™) (neo), gentamycin (aac3 or aacC4), hygromycin B (aphIV, hph, hpt), kanamycin (val), methotrexate (DHFR $mtx^R$), penicillin and other β-lactams (β-lactamases), streptomycin or spectinomycin (aadA, spec/strep), and tetracycline (tetA, tetM, tetQ); genes conferring tolerance to herbicides such as aminotriazole, amitrole, andrimid, aryloxyphenoxy propionates, atrazines, bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, urea; including genes encoding enzymes that provide resistance or tolerance to herbicides as acetyl CoA carboxylase (ACCase), acetohydroxy acid synthase (ahas), acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acteyl transferase (pat, bar), phytoene desaturase (crtI), prenyl transferase, protoporphyrin oxidase, the psbA photosystem II polypeptide (psbA), SMM esterase (SulE) superoxide dismutase (sod); genes that may be used in auxotrophic strains or to confer other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene;

or optionally wherein a reporter protein is selected from the group consisting of lacZ; a luciferin/luciferase gene; a beta-glucuronidase gene (GUS), or a gene encoding a blue, cyan, green, enhanced green, red, yellow, or photoconverting fluorescent protein, or a variant thereof.

Embodiment 7

The vector of Embodiment 6, wherein the vector further comprises one or more of: an origin of replication, one or more sequences for promoting integration of the expression cassette into the host genome, a sequence of embodiment 3 that comprises a terminator, or an additional gene, wherein the additional gene encodes an antisense RNA, a micro-RNA, an shRNA, a ribozyme, structural protein, an enzyme, a transcription factor, or a transporter.

Embodiment 8

A eukaryotic cell comprising an isolated or recombinant nucleic acid molecule or expression cassette of any of Embodiments 1-4, or a vector of any of Embodiments 5-7.

Embodiment 9

The eukaryotic cell of Embodiment 8, wherein the eukaryotic cell is an algal cell, optionally, a species of *Bacillariophyceae* (diatoms), *Bolidomonas*, *Chlorophyceae* (green algae), *Chrysophyceae* (golden algae), *Cyanophyceae* (cyanobacteria), *Eustigmatophyceae* (pico-plankton), *Glaucocystophytes*, *Pelagophyceae*, *Bolidophyceae*, *Prasinophyceae* (pico-plankton), *Raphidophyceae*, *Rhodophyceae* (red algae), *Synurophyceae* and *Xanthophyceae* (yellow-green algae), or is of a genus selected from the group consisting of: *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*.

Embodiment 10

The eukaryotic cell of Embodiment 8, wherein the eukaryotic cell is a heterokont cell, optionally, a species the order Chytridiomycota or Labyrinthulales, preferably a species of *Thraustochytrid, Thraustochytrium, Labrynthula, Labyrinthuloides, Japonochytrium*, or *Schizochytrium*.

Embodiment 11

A method of transforming a eukaryotic cell comprising introducing an expression vector of any of embodiments into a eukaryotic host cell and selecting a transformant, preferably wherein the eukaryotic host cell is a fungal, algal, heterokont, or plant host cell optionally wherein the eukaryotic host cell is a species of *Bacillariophyceae* (diatoms), *Bolidomonas, Chlorophyceae* (green algae), *Chrysophyceae* (golden algae), *Cyanophyceae* (cyanobacteria), *Eustigmatophyceae* (pico-plankton), *Glaucocystophytes, Pelagophyceae, Bolidophyceae, Prasinophyceae* (pico-plankton), *Raphidophyceae, Rhodophyceae* (red algae), *Synurophyceae* and *Xanthophyceae* (yellow-green algae), *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria*, or *Volvox*, optionally the species *Nannochloropsis gaditana, Nannochloropsis granulata, Nannochloropsis limnetica, Nannochloropsis maritima, Nannochloropsis oceanica, Nannochloropsis oculata*, or *Nannochloropsis salina*.

Embodiment 12

A method for detecting promoter activity in a heterokont or algal cell, the method comprising: (1) transforming a heterokont or algal cell culture with a vector that comprises a known or putative promoter sequence operably linked to a gene encoding a fluorescent protein and a selectable marker gene to produce a transformation culture; (2) selecting transformed cells; and (3) measuring fluorescent protein signal(s) of the transformed cells, wherein the selection of a transformation culture comprises plating the transformation culture on agar containing a selection agent and allowing algal colonies to grow on agar, further optionally wherein the measurement of fluorescent protein signal(s) comprises measuring fluorescent protein signal(s) produced by one or more algal colonies on the agar plate to identify at least one algal colony that includes an expression vector that comprises a promoter.

Embodiment 13

The method of Embodiment 12, wherein one or more of the following is satisfied:

the transformation culture is analyzed or sorted by flow cytometry before selecting a transformation culture;

the putative promoter sequence is derived from the nuclear genome of an algal or heterokont species; or the transformants are selected on nitrogen replete media.

EXAMPLES

The following examples are merely illustrative, and do not limit this disclosure in any way.

Example 1

Strain and Cultivation

*Nannochloropsis gaditana* was obtained from the CCMP culture collection (CCMP1894) and assigned an internal name of WT-35. Cultures were grown in 50 mL of PM024 medium in 250 mL shake flasks at 100 rpm on a 0.75 inch orbital shaker under 50 μE, constant light, 1% $CO_2$ at 25° C. Light intensity was measured using LI-COR Light Meter, LI-250A. PM024 was prepared by dissolving 35 g of Instant Ocean salts (Aquatic Eco Systems, Apopka, Fla.) and 200 mL of f/2 50× concentrate (Sigma G0154) in milliQ filtered water to make 1 liter. The solution was filter sterilized by passage through a 0.2 micron bottle top filter (Corning #430513). Zeocin was supplied at 5 μg/mL. Cell density was measured by flow cytometry using an Accuri C6 flow cytometer with the following settings for *Nannochloropsis*: density ≤$10^7$ cells/mL; minimum sample size 25 μL; count 10,000 events; 10 micron core size (slow fluidics); threshold set at 30,000 on FSC-H; gate on chlorophyll peak in FL-3 channel.

Example 2

Identification of Promoter and Terminator Sequences

Transcript profiling was used to identify novel promoter and terminator regulatory regions. WT-35 was grown in nitrogen replete (7.1 mM $NH_4Cl$) and nitrogen deplete (0 mM $NH_4Cl$) culture media. Cultures were grown in three conditions—nitrogen replete seed culture (condition 1) and cultures incubated subsequently in nitrogen replete (condition 2) or deplete (condition 3) conditions for two days (Table 3). Total RNA was collected from condition 1 cultures on day 0 and from conditions 2 & 3 cultures on day 2.

RNA samples were sequenced by Ambry Genetics (Aliso Viejo, Calif.) after poly-A purification and fragmentation. mRNA was sequenced using sequencing-by-synthesis (a.k.a. Solexa sequencing) to generate 50 bp singleton reads using the mRNA-Seq procedure (described in Mortazavi et al. (2008) *Nature Methods* 5:621-628), indexing the nine samples in two lanes of the Illumina Genome Analyzer IIx. Each sample yielded an average of two million mappable reads, which were aligned to the *N. gaditana* reference genome sequence using CLC Genomics Workbench software. Expression levels were computed for every annotated gene normalized for gene length and total number of mappable reads per sample, and reported in mean RPKM units for every sample. Mean RPKM is a measure of relative transcriptional levels that normalizes for differences in transcript length.

The RNA-Seq Analysis tool in CLC Genomics Workbench was used to map the reads in each sample to 19,502 annotated genes. Expression levels in RPKM were calculated for every gene and every condition using standard parameters allowing for reads to map up to 50 bp upstream and downstream from every gene. Differential expression between conditions was calculated using Baggerley's test on the proportions of total number of mapped reads per sample per gene, with a false discovery rate of 0.05 or lower considered a statistically significant fold-change. The mean level of transcript abundance was 128 to 150 RPKM, with a range from 0 to almost 10,000. In order to identify constitutive promoters for use in heterologous expression, the dataset from this experiment was queried using genes typically involved in basic cellular functions, choosing those whose relative expression levels ranged from the mean to approximately 1,500 RPKM and whose expression levels did not change substantially across the three conditions (Table 3).

TABLE 3

Genes with constant expression level in *Nannochloropsis*

| Translation description | Condition 1 mean RPKM | Condition 2 mean RPKM | Condition 3 mean RPKM | GFP expression vector |
|---|---|---|---|---|
| Enolase, C-terminal TIM barrel domain | 1,209 | 899 | 887 | p05133 |
| RuBisCo accessory protein AAA type ATPase, cbbX | 532 | 574 | 517 | p05134 |
| Eukaryotic initiation factor 4-AIII | 155 | 151 | 203 | p05136 |
| Replication factor A protein 3 | 336 | 215 | 260 | p05138 |
| Translation initiation factor eIF3 subunit | 169 | 116 | 177 | p05140 |

Example 3

Cloning and Vector Constructions

Restriction enzymes, ligase, and polymerase (Phusion) were purchased from New England Biolabs.

Figure 3A:
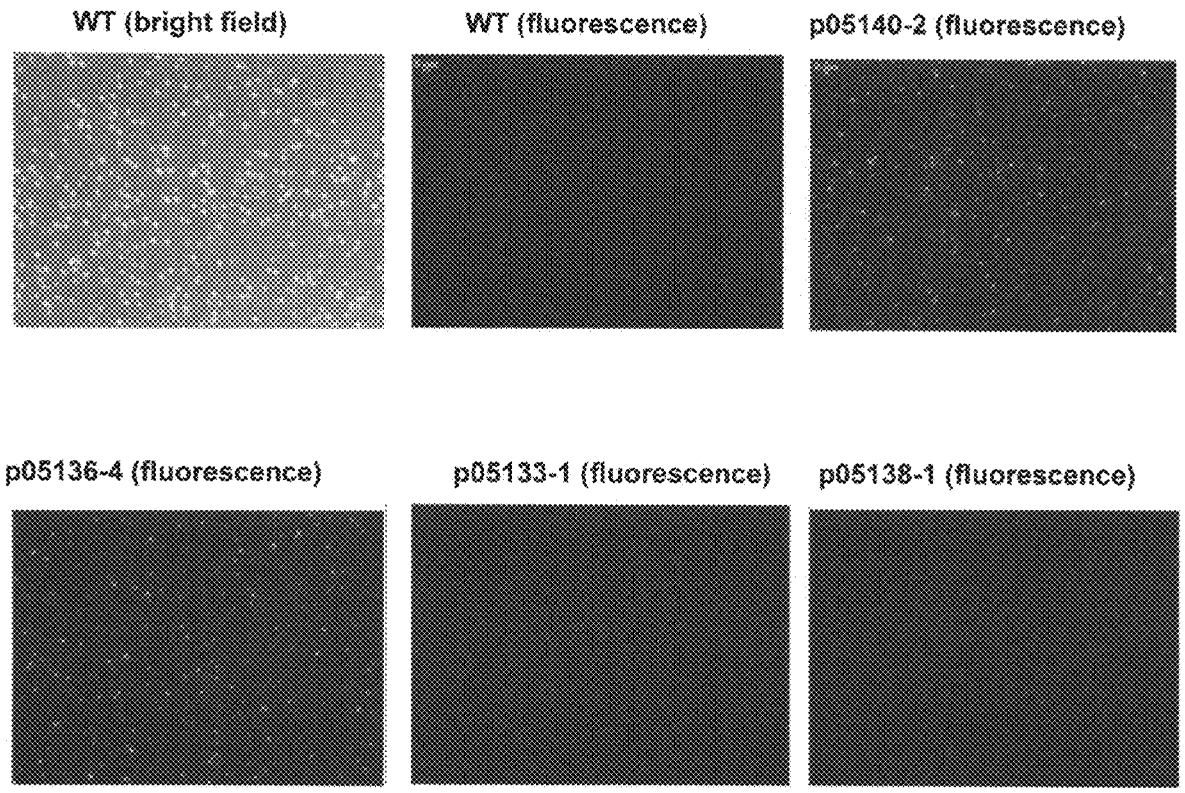
FIG. 3A is a representation of fluorescent microscopic images analyzing GFP signal for several isolates. Data shown were collected from culture that is three weeks post-inoculation from cell patches on agar plates.
Figure 3B:
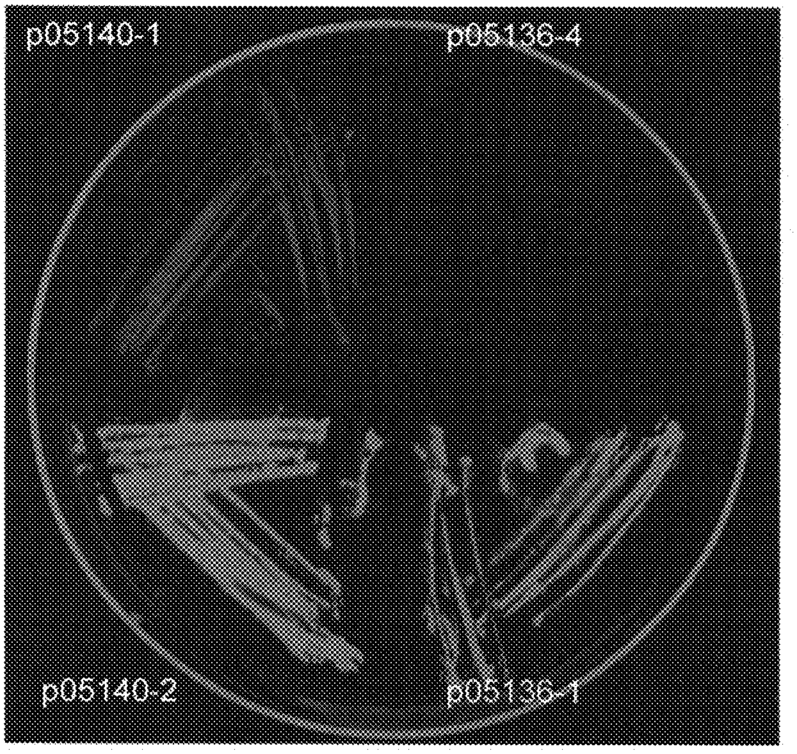
FIG. 3B is a fluorescent image detecting GFP activity in colonies spread on a PM024 agar plate using a FluorolImager. GFP expressing *N. Gaditana* was incubated on an agar plate with 5 μg/ml zeocin.

The Simian virus 40 (SV40) promoter-5'-UTR and 3'-UTR-terminator sequences were designed to control expression of the ble gene encoding Zeocin resistance, to form the SV40-ble selectable marker in pBL108 (FIG. 3B).

Vectors were constructed by in vitro recombination using Gibson's cloning method (Gibson et al. (2009) *Nat. Methods* 6:343-345). The DNA fragments were synthesized or PCR-amplified to have overlapping ends, after which a T5 exonuclease is used to remove nucleotides from the 3' ends, exposing the overlaps. After annealing, the gaps were repaired by Phusion polymerase and T4 ligase. All isolates were checked by DNA sequencing to ensure the correct sequence was cloned.

p05140, in which the eIF3 promoter fragment (SEQ ID NO:9) and terminator fragment (SEQ ID NO:10) are joined to TurboGFP (FIG. 1), was created by first amplifying the eIF3 promoter and terminator sequences from the *N. gaditana* genome and the TurboGFP coding sequence from pTurboGFP-B (Evrogen, Moscow, Russia). Amplification was carried out with PCR primer sets that included a set of complementary sequences in the 5' ends of the eIF3 promoter reverse primer and the TurboGFP forward primer and a different set of complementary sequences in the 5' ends of the TurboGFP reverse primer and the eIF3 terminator forward primer. The ends of the three amplicons were then digested with T5 exonuclease, annealed together at 50° C., repaired with Phusion polymerase, and ligated with T4 ligase to form an eIF3/TurboGFP expression cassette. The plasmid p108 and the newly constructed expression cassette were then digested with SfoI and SalI and joined to form p05140. The plasmid map and an illustration of the assembly are shown in FIG. 1. Plasmids p05133, p05134, p05136, p05138, and p05140 (see Table 3) were prepared in a substantially similar manner.

Example 4

Transformation and Evaluation of Expression

Vectors were linearized by restriction enzyme digestion and the digested DNA was purified by phenol-chloroform extraction. A logarithmic-stage culture of *Nannochloropsis gaditana* was washed three times with 384 mM sorbitol and resuspended in 384 mM sorbitol at $1\times10^{10}$ cells/mL. 100 ul of the washed cells were mixed thoroughly with 5 μg of linearized plasmid DNA in an ice-chilled 2 mm electroporation cuvette. The electroporation was conducted with BioRad GenePulser set at 50 μF capacitance, 500Ω resistance, 2.2 kV. After electroporation, 1 mL of 384 mM sorbitol was added and cells were transferred to 10 mL of PM024 media. The culture was incubated at 25° C. overnight in dim light (5 uE/$m^2$/s). $5\times10^8$ cells were spread onto PM024 agar media in 80 mm polystyrene petri dishes with 5 μg/mL Zeocin. The cells were incubated at room temperature under constant light (70-80 μE/$m^2$/s) for three weeks. Transformants were patched on PM024 agar with 5 μg/mL Zeocin and a liquid suspension culture was initiated in PM024 with 5 μg/mL Zeocin.

Example 5

Evaluation of Promoter Activity

Figure 2:
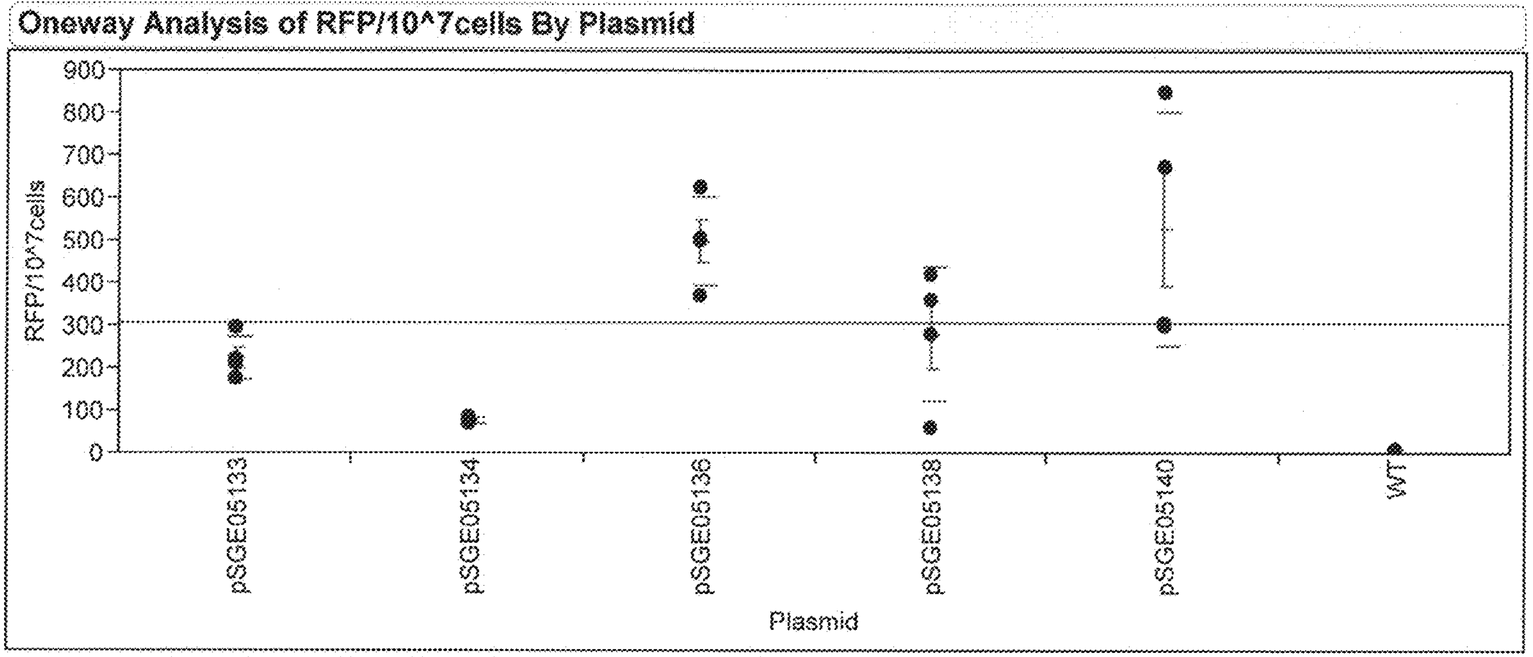
FIG. 2 is a representation of fluorescence spectroscopy measuring GFP signal from four independent transformants using a fluorescence microplate reader.

Promoter test vectors were transformed into *Nannochloropsis gaditana* cells (WT-35). Four single colony isolates from each transformation were patched to a new plate, and then used to start liquid cultures in PM024 medium. The GFP fluorescence of the culture was measured using a SpectraMax M5 fluorescence microplate reader (Molecular Devices, excitation 480 nm, emission 520 nm, autocutoff=490 nm) The results, provided in FIG. 2, show that all of the promoter constructs (p05133, p05134, p05136, p05138, and p05140) resulted in expression of the fluorescent protein gene, although relative GFP signal obtained from the plate reader was found not to be correlated to the RPKM levels identified by transcription profiling. Cultures transformed with p05136 (containing SEQ ID NO:5 as the promoter/5'UTR and SEQ ID NO:6 as the terminator/3'-UTR (eukaryotic initiation factor 4-AIII)) and p05140 (containing SEQ ID NO:9 as the promoter/5'UTR and SEQ ID NO:10 as the terminator/3'UTR (translation initiation factor eIF3 subunit gene)) (see Table 3) showed the highest signal, although the transcription level for these promoters was lower than others tested. (Different isolates carrying the same construct are donated with a dash plus a number, e.g., p05136-1, p05136-2, etc.))

The GFP signal for several isolates was examined using fluorescence microscopy (Zeiss Axio fitted with LED and filter set 69 was used, excitation 452-458 nm, emission 510-610 nm). GFP signal was easily detected in isolates with the highest activity (p05140-2 and p05136-4) (FIG. 3A). When streaked on agar plates, GFP fluorescence was easily detectable and highest in the p05140-2 isolate (Fluor Chem® Q from Alpha Innotech, using the Cy2 filter and blue light source, excitation at 475 nm and emission at 537 nm) (FIG. 3B), although the p05140-1 isolate showed strikingly lower level of GFP fluorescence. Surprisingly, fluorescence from the p05136-4 isolate was undetectable, although it had been visible under fluorescent microscopy. This was a consequence of the instability detected in some strains.

The fluorescence signal of the population of cells from the isolates showing the highest activity was examined by flow cytometry (Accuri C6 flow cytometer, GFP fluorescence was detected using the FL1 channel with an excitation of 488 nm and an emission of 530 nm). One of these isolates (WT-35/p05140-2) showed a normal distribution of GFP activity, which indicated a consistent level of GFP expression among the cell population. For the other three, the GFP activity per cell showed a wide distribution. These populations were passaged twice in the presence and absence of Zeocin to evaluate the GFP expression stability. The strain with the highest consistency (WT-35/p05140-2) maintained the consistent and high level of expression (~80 times above the untransformed control) even in the absence of selection for the introduced DNA. Another one of the strains (WT-35/p05136-2) appeared to lose cells with highest and lowest expression levels between P1 and P2, resulting in a population with increased consistency of expression, but lower overall activity. This lower activity was stable in the absence of Zeocin selection. The other two lines, (WT-35/p05136-1) and (WT-0035/p05140-1) continued to show a broad distribution, and the absence of Zeocin selection correlated with loss of GFP fluorescence in these isolates.

Example 6

Evaluation of Stable Transformant by Southern

Southern blots were performed in order to evaluate the structure of the stable transformant p05140-2 and two isolates from a transformation with p108, i.e. p0584 and p0585. Genomic DNA was digested using a restriction enzyme and separated on an agarose gel in TAE buffer. A ble gene probe was randomly labeled with digoxigenin-dUTP according to manufacturer's instructions (DIG High Prime DNA Labeling and Detection Starter Kit I, Roche Cat. No. 11 745 832 910). DNA was transferred from the gel to a charged nylon membrane (Roche Cat #1417240) by capillary action in the presence of 0.4M NaOH. The damp membrane was cross-linked at 1200 microjoules with UV for 30 sec. The membrane was then incubated at 42° C. in pre-hybridization buffer before adding the denatured probe. Hybridized membranes were washed 2 times for 15 min. each in 2×SSC, 0.1% SDS and then 2 times for 15 min. each in 0.5×SSC, 0.1% SDS. The membrane was then blocked, incubated in the presence of anti-digoxigenin-alkaline phosphatase coupled antibody, and washed before detection of the probe-antibody using NBT/BCIP.

Judging from the size of the detected band, transformants arising from both p108 and p05140 contain the vector integrated as concatemers. The maintenance of a circularized plasmid would generate the same result and cannot be ruled out by this experiment. However, the strains had been passaged for multiple generations, so this possibility is unlikely. Head-to-tail concatemers are the most common multimer detected in random integration into eukaryotic genomes ranging from mouse (Schneider & Wolf (2005)

*Analytical Biochem.* 344:1-7) to *Chlamydomonas* (Dent et al. (2005) *Plant Phys.* 137:545), although other arrangements (including head-to-head and various types of rearrangements) are possible (Folger et al. (1982) *Mol. & Cell. Biol.* 2:1372).

The p108 transformants showed bands of unique size in addition to the concatemer which may result from a vector-genome junction. Genome walking with RAGE (Cormack & Somssich (1997) *Gene* 194:273-276) was used to identify the insertion junction of the integrated plasmid and to examine the structure of the insertion in the WT-35 genome. Genomic DNA was restriction digested then ligated to an adaptor, followed by PCR amplification using a vector-specific primer and a primer for the adaptor. Products were gel purified and sequenced.

The data show small gains or loss of DNA at the insertion junction. For p0584, 77 bp of the vector at the linearization site was not present. For p0585, there was a small insertion of unknown DNA at the junction, whereas p05140 plasmid appeared to be cleanly integrated without any loss at the insertion site.

Putative gene regulatory elements (promoter-5'-UTR/3'-UTR-terminator) regions were identified by transcriptomics (transcript profiling) and cloned from the *Nannochloropsis gaditana* genomic DNA. Using Turbo-GFP as a reporter gene, five different promoter/terminators were identified that expressed GFP at various levels detectably above an untransformed control.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the term “or” as used in a phrase such as “A or B” herein is intended to include “A and B”, “A or B”, “A”, and “B”. The singular forms “a,” “an,” and “the” may be intended to include the plural forms as well, unless the context clearly indicates otherwise. The terms “comprises,” “comprising,” “including,” and “having,” are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. An expression cassette comprising a nucleic acid sequence encoding a polypeptide or a functional RNA operably linked to a heterologous promoter, wherein the heterologous promoter comprises a nucleotide sequence having at least 95% identity with SEQ ID NO: 9.

2. The expression cassette according to claim 1, wherein the nucleic acid sequence encoding a polypeptide or a functional RNA is operably linked to a heterologous terminator, wherein the terminator comprises a nucleotide sequence having at least 95% identity to SEQ ID NO: 10.

3. The expression cassette according to claim 1, wherein the nucleic acid sequence encoding a polypeptide or a functional RNA is operably linked to a terminator comprising a nucleic acid sequence having at least 95% identity to SEQ ID NO:2.

4. The expression cassette according to claim 1, wherein the nucleic acid sequence encoding a polypeptide or a functional RNA encodes (a) protein associated with lipid biosynthesis, (b) a lipase, (c) a protein that participates in photosynthesis, (d) a protein associated with carbon fixation, (e) a transporter protein, (f) a dehydrogenase, (g) a transcription factor, (h) a cell signaling protein, or (i) a functional RNA.

5. The expression cassette according to claim 4, wherein the nucleic acid sequence encoding a polypeptide or a functional RNA encodes a functional RNA selected from the group consisting of an antisense sequence, a micro RNA, an shRNA, an siRNA, and a ribozyme.

6. A vector comprising the expression cassette according to claim 1.

7. The vector according to claim 6, further comprising a selectable marker or reporter gene.

8. The vector according to claim 6, wherein the nucleic acid sequence encoding a polypeptide or a functional RNA is operably linked to a terminator comprising a nucleic acid sequence having at least 95% identity to SEQ ID NO:2.

9. The vector according to claim 6, wherein the nucleic acid sequence encoding a polypeptide or a functional RNA encodes a selectable marker or reporter.

10. The vector according to claim 9, wherein the nucleic acid sequence encoding a polypeptide or a functional RNA is selected from the group consisting of a gene conferring resistance to an antibiotic, a gene conferring resistance to an herbicide, a gene encoding acetyl CoA carboxylase (ACCase), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS (aroA), a gene encoding a non-class I/II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acteyl transferase, a gene encoding phytoene desaturase, a gene encoding prenyl transferase, a gene encoding protoporphyrin oxidase, a gene encoding superoxide dismutase, arg7, his3, hisD, hisG, manA, nit1, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene, an R-locus gene, a tyrosinase gene, lacZ, an alkaline phosphatase gene, an α-amylase gene, a horseradish peroxidase gene, an α-galactosidase gene, a luciferin/luciferase gene, a beta-glucuronidase gene (GUS), and a gene encoding a fluorescent protein.

11. The vector according to claim 6, wherein the vector includes at least one origin of replication.

12. A method for transforming a eukaryotic cell comprising: introducing the vector according to claim 6 into the eukaryotic cell; and selecting for a transformant.

13. The method according to claim 12, wherein the eukaryotic cell is selected from the group consisting of a fungal cell, a heterokont cell, an algal cell, and a plant cell.

14. The method according to claim 13, wherein the eukaryotic cell is an algal cell.

15. The method according to claim 14, wherein the algal cell is selected from the group consisting of species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetraselmis, Thalassiosira, Tribonema, Vaucheria, Viridiella, Vischeria*, and *Volvox*.

16. The method according to claim 15, wherein the algal cell is a *Nannochloropsis* algal cell.

17. A method for transforming a eukaryotic cell comprising: introducing the vector according to claim 9 into the eukaryotic cell; and selecting for a transformant.

18. The method according to claim 17, wherein the eukaryotic cell is an algal cell.

19. The method according to claim 18, wherein the algal cell is selected from the group consisting of species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*.

20. The method according to claim 18, wherein the algal cell is a *Nannochloropsis* algal cell.

21. A eukaryotic host cell transformed with the vector according to claim 6.

22. The eukaryotic host cell according to claim 21, wherein the eukaryotic host cell is an algal cell.

23. The expression cassette according to claim 2, wherein the terminator is SEQ ID NO:10.

24. The expression cassette according to claim 1, wherein the promoter comprises SEQ ID NO:9.

25. The expression cassette of claim 1, wherein the nucleic acid sequence encoding a polypeptide or a functional RNA is operably linked to a terminator comprising SEQ ID NO:2.

26. The expression cassette of claim 1, wherein the nucleic acid sequence encoding a polypeptide or a functional RNA is operably linked to a terminator comprising a nucleotide sequence having at least 95% identity to SEQ ID NO:4.

27. The expression cassette of claim 1, wherein the nucleic acid sequence encoding a polypeptide or a functional RNA is operably linked to a terminator comprising a nucleotide sequence having at least 95% identity to SEQ ID NO:6.

28. The expression cassette of claim 1, wherein the nucleic acid sequence encoding a polypeptide or a functional RNA is operably linked to a terminator comprising a nucleotide sequence having at least 95% identity to SEQ ID NO:8.

29. The expression cassette according to claim 1, wherein the nucleic acid sequence encoding a polypeptide or a functional RNA is operably linked to a terminator comprising SEQ ID NO: 4.

30. The expression cassette according to claim 1, wherein the nucleic acid sequence encoding a polypeptide or a functional RNA is operably linked to a terminator comprising SEQ NO:6.

31. The expression cassette according to claim 1, wherein the nucleic acid sequence encoding a polypeptide, or a functional RNA is operably linked to a terminator comprising SEQ ID NO:8.

32. The expression cassette according to claim 1, wherein the nucleic acid sequence encoding a polypeptide or a functional RNA is operably linked to a terminator comprising SEQ ID NO: 10.

33. The vector according to claim 6, wherein the nucleic acid sequence encoding a polypeptide or a functional RNA is operably linked to a terminator, wherein the terminator comprises a nucleic acid sequence having at least 95% identity to SEQ. ID NO:4.

34. The vector according to claim 6, wherein the nucleic acid sequence encoding a polypeptide or a functional RNA is operably linked to a terminator comprising a nucleic acid sequence having at least 95% identity to SEQ NO:6.

35. The vector according to claim 6, wherein the nucleic acid sequence encoding a polypeptide or a functional RNA is operably linked to a terminator comprising a nucleic acid sequence having at least 95% identity to SEQ ID NO:8.

36. The vector according to claim 6, wherein the nucleic acid sequence encoding a polypeptide or a functional RNA is operably linked to a terminator comprising a nucleic acid sequence having at least 95% identity to SEQ ID NO:10.

37. The vector according to claim 6, wherein the promoter comprises SEQ ID NO:9.

* * * * *

SEQUENCE LISTING

```
<160> NUMBER OF SEQ ID NOS: 16

<210> SEQ ID NO 1
<211> LENGTH: 1000
<212> TYPE: DNA
<213> ORGANISM: Nannochloropsis gaditana

<400> SEQUENCE: 1

agcatgcgga tgacaggctt aacaaccagt attacacgtt taccgcagct cacttaccca     60

ttgttatacc caatgttacc agtactacag taatgcggtt tcgattgcgt gtggatagtg    120

ttgctgcatt tttgccggca cccggggcgg caaccatcat catcatcatc atcatggtcg    180

ttacaggatt tcttagccct ttcccacctc agccgggaaa aattgtccct ttgattgcag    240

aaattgatct tcaaatgttt tgattgtctg tcgaaacgta tgttacagta gcaggtctct    300

gagatccgta gatgcgagcc cagtgcccag aatcatgtta tcaacctcct gcaagccagg    360

ctgcagggac gtggcgggct tggacatgca tggatcttga acaacaaaac aaggtcaagc    420

tgactgcaag tctttgaaag aatagcggga taaacacagc aggtttgtac gacactacag    480

gcctcgtgaa atggccatat tcctacattc tgtgaacatc acgagattta cgatcatgct    540

tttagcgatc aagacgagtg atctgaaatc gtggagcgac acatgatgtg caacgtcgaa    600

tcccacgcac actcgtgtcg cgtcgcttaa aagctcactt cttgtaagca ctaggagaag    660

gaattgcttt ctgtgttcac cggtcacatt tcggcatggt tcgaagcggc agtgtagaag    720

tcagtgtgga tcgtaggaag gggcactata gactgagcgg cctgccccccg ccttacaaac    780

ggagccccga cgacgcatgc gccgagacga atgatggctg atccccccgta tcaggacgcg    840

tcgctcttcg tctcgtgctt gtcctgatgc cacctgaacc cgcaacacgt ccggtctaca    900

catttataca ggtcttccaa ttcctgtcga tgaggacatc gtccgctctg tgtctcctcc    960
```

```
tggggtccct ctcttactcg tcctgtacgt tgtgttttgt                          1000


<210> SEQ ID NO 2
<211> LENGTH: 998
<212> TYPE: DNA
<213> ORGANISM: Nannochloropsis gaditana

<400> SEQUENCE: 2

attttaatca gcctacacga tgggtatgca tgaggatttg acggatcagc gcccgaggtg      60

tgtgtgataa ggcggaaatg actctgccta tctggcgaga aacggaagag taccgaaaaa     120

cagctttcgt gtgtttttgt gcgcctcaca tgcggtgcat ctgcattgag agctctgtgt     180

tgatgtcaat gcactgtcgt atgtgtaacg aggctatatt taccggaatc ttgaatctcg     240

aatcgcgtgc agctctaagt acgcctcgaa agggatgtca ctttgtagcc tgcagctctc     300

agtaggtctc gcaagagata ttacttagta ttgtattctt accgggttgt ggcaagagcg     360

ttacgagaag gccgtgtacg acatcattga ggtgagtgaa agtcaggatt gtgctttatg     420

atatgatgtg tctctataca accgcctgga tatctagtca ggaaagatag atgaggaaga     480

cgaatcatga agaagtatga tacatggaaa aatgtgtact gctcgagttc tgagagcttt     540

gttttctgct gtccatctct tgtcgttatt cattgaaaca ttttggcatc gttcgtcatt     600

ttggtccaca taagtcatac ttgcttcctg gtgagccatg cgtattgctg ctgcttttca     660

gtgtacgcgc atgcaacctt tcacgtgtgc agatctccgt tacgcttccc tacagccttc     720

actttttggc ttcgaccaat tagtcacgtc tcaacgcgct ttaaattcgg cctccgcgta     780

tgaggcaaca catgatgcat ggctccatcc agagaggaaa cctccatccc aaaaatacac     840

ccacacttcg aaacttctgt ctaaattttc acggtcccaa tcgcgatgct caaagcgtag     900

cccactgcat ccgtgggata gctggttcta catttgtgca cagacctcct tgtgcgccct     960

gcaccctttc tattccgtga agtccatcct gtccacct                             998


<210> SEQ ID NO 3
<211> LENGTH: 512
<212> TYPE: DNA
<213> ORGANISM: Nannochloropsis gaditana

<400> SEQUENCE: 3

tgcttgacgg agcgggagca agggcccgaa tcctcccaaa ctttcccctg tgcgttgtcc      60

ggtaaaagta ttaattagtt gcccggcatg agccacagcc tgccgcggta ccacctcaaa     120

acatcgcacg cgccgactcg caggggacgg cgtggtgtgg gcatcgaggg tgtctctctc     180

atcataagtg cccgcgaggc tcgcctacag cggactgcca tggcgatcct ggtcaatgca     240

tgagacgctg agacatacgc ttcctacgtg tgcagggcga tggtggacac gatgcggtac     300

cagtcgcacg tttgagggtt attgtgcctc tgtttgtggg attactcggg taccaggtgt     360

aggaaagaac gcgcgagcac ggcaacaaaa agatcttgtc ctggtctcac ccttcttctg     420

cttcatgcat actacactcc cacgcttgcg ttccattttc ggcatcataa tgcacagact     480

caaccgcata cactggaaca atggtgacga cg                                   512


<210> SEQ ID NO 4
<211> LENGTH: 474
<212> TYPE: DNA
<213> ORGANISM: Nannochloropsis gaditana

<400> SEQUENCE: 4
```

-continued

```
tgccgatcgc gtgtagatcg tataagctta tgtgcggtcc atgcttgtgc gtgatttccc     60

gcaatctcca tgtccaccac tacgggctgt cggagggtgt gtactcaata tttctctctg    120

gaacgtatgt cgtgcggtag gggacgatag gggatgcgct tgggtttgcc agatacgtgt    180

tatcgacgat gaaagattga tacggtcaaa ataattgaac ttttgtagtc gtgtagagac    240

aagggccagg gagatagtgg gtagcgtcgc ttgagctctc tttccttaga cacaacgatg    300

tccgcaagga acaccacggt atgtgtgatt gattggaaca gcgtatggcg gaaaggaatt    360

gaaggaccga gggaagagag aaacgagttt gaccaatgag ggatgagctg tgattttttcc    420

ccttttgttg cactttattc tcatgtatgc tttctcttcg acaaaattgt tgtc          474


<210> SEQ ID NO 5
<211> LENGTH: 823
<212> TYPE: DNA
<213> ORGANISM: Nannochloropsis gaditana

<400> SEQUENCE: 5

ggcataaagg acggcaagga aaagaaaaga aagaaagaaa aggacactta tagcatagtt     60

tgaagttata agtagtcgca atctgtgtgc agccgacaga tgcttttttt ttccgtttgg    120

caggaggtgt ggggatgtcg aagaccagtc cagctagtat ctatcctaca agtcaatcat    180

gctgcgacaa aaatttctcg cacgaggcct ctcgataaac aaaactttaa aagcacactt    240

cattgtcatg cagagtaata actcttccgc gtcgatcaat ttatcaatct ctatcatttc    300

cgcccctttc cttgcataga gcaagaaaag cgacccggat gaggataaca tgtcctgcgc    360

cagtagtgtg gcattgcctg tctctcattt acacgtactg aaagcataat gcacgcgcat    420

accaatattc ttcgtgtacg gagatgaaga gacgcgacac gtaagatcac gagaaggcga    480

gcacggttgc caatggcaga cgcgctagtc tccattatcg cgttgttcgg tagcttgctg    540

catgtcttca gtggcactat atccactctg cctcgtcttc tacacgaggg ccacatcggt    600

gcaagttcga aaaatcatat ctcaatcttc agatcctttc cagaaacggt gctcaggcgg    660

gaaagtgaag gttttctact ctagtggcta ccccaattct ctccgactgt cgcagacggt    720

ccttcgttgc gcacgcaccg cgcactacct ctgaaattcg acaaccgaag ttcaatttta    780

catctaactt ctttcccatt ctctcaccaa aagcctagct tct                      823


<210> SEQ ID NO 6
<211> LENGTH: 175
<212> TYPE: DNA
<213> ORGANISM: Nannochloropsis gaditana

<400> SEQUENCE: 6

gagggggggct cgagagggag aggggtgtgt catatgaggg cggcggggaa ttcgtgtgtg     60

aaaggaaagc atgagtcgat aaaggggggg gtggagcgag acaaagaaga aacgggggtc    120

gatagcgctg atccaaagcg tcgtctcagc tttcttttct cgcgacgcca acctc         175


<210> SEQ ID NO 7
<211> LENGTH: 1000
<212> TYPE: DNA
<213> ORGANISM: Nannochloropsis gaditana

<400> SEQUENCE: 7

caaggattga agcgtttgtc gtactctggg tagacccaat gctcaccaac tgtcgtcttt     60

cgattgtaaa tgtgtggtaa tgacggaagg taagatgacg caaaggtgag gttgggagga    120

ggcttcagta tgagatttga ttcatcgccc ttaagaggat aaatccggga tacattcata    180
```

ctaatgcttg aaaaatagtt gtactcgatc acctacagta tttctccaag tttttcgtcc 240
attgacgatt ggttccagat gccacgaatc aagcctgaat cccaccccgc attatcgcat 300
ctcacctctc acctcgggca ttgcacattc cgcactctct cttgccattt tcatcccgtc 360
aggtttttag ggcgggcaat ctctgtcagg cacatttttt taataaaaag gccacatgcg 420
agtgacgcgc tatgttcgca ccggggcttc gtggcctaga tctaagtccc cccaaatatg 480
ttgtcgcctt gaccagaaag ccctttagtc cgacctcaac cacacgtaga cgggactgcg 540
gtcggtcggt cctcgtaatt atatcaagcc attttttgag cactgcaagc ttaaatttgt 600
gccgcaccgt gaaaatgatt taaaatataa ttaatcacca tattacgccc ttgaagtatt 660
ctggaatgct gttacaaagt cataatatct gaatagccga cggattggga gggctggaag 720
gtttgctcga ggcggcaaac gccaaaaagc gagaagcgcg gtctccgctc ccttcgtccc 780
gtcggggggg gggcgaggtt ctttctgcct tctggtgtgt ccgtgccgac acgaaatacg 840
atgggtggaa agcttgatcg tacaatctgg caatctataa tgtgattgtc gtcgctcaaa 900
cgtaagctct gtatctcaag aatggtccgc gcgccttctt tgggtcaccg actctctctc 960
tacctctcct cacagaaaac tcaccacaat tgtgtcggca 1000

<210> SEQ ID NO 8
<211> LENGTH: 337
<212> TYPE: DNA
<213> ORGANISM: Nannochloropsis gaditana

<400> SEQUENCE: 8
agtccgggta accagaggac gtggcatgta gacaagcacg ttcattttca tatacatggg 60
caacgaagga gagaggtctg gtggtagagt ggtagagcaa aagaggaaag catgaaatga 120
actgtaggga gtcggaaaaa caaatttgcg aacaaaccac gtaaacaaag aagctggtca 180
agaagtcgcc atgaatcctt tgatagacgc taatacgggc aagcggacaa gaacttgtcc 240
tcatttttcc cagctgtgtg gtatgattgg ccaatgaggt ccaaatctct gattgggcct 300
catgaagccc catgtcgtaa agcttgtgtc gctcctt 337

<210> SEQ ID NO 9
<211> LENGTH: 1000
<212> TYPE: DNA
<213> ORGANISM: Nannochloropsis gaditana

<400> SEQUENCE: 9
tcataatcaa agatgagcca gccacgaagc taccggagaa ttctgtaaga aaaatgttta 60
aagttgaaaa tgctaacagt gaagtgatat cctttttaa tggagtgttg aggtgaagtc 120
tagcatcgta ggggaaaaca ggattctgtg tcttccattc tactccttga taaagcgaag 180
aaatccgaca aaaccaaaga gattgttcaa gtttaagatt tgtaagcgta caactatgaa 240
cttcttctct ttgtaggcct gagtggtcgt atgcatacga ttcatgaagt gaatcagtat 300
cgctggattt tgcttaggag taaagcacaa ctaagaaaat atgctgcctg gcaggcatcc 360
tgagacatga ggcaagcgac gtagcaattg aatcctaatt taagccaggg catctgtatg 420
actctgttag ttaattgatg aaccaatgag ctttaaaaaa aaatcgttgc gcgtaatgta 480
gttttaattc tccgccttga ggtgcggggc catttcggac aaggttcttt ggacggagat 540
ggcagcatgt gtcccttctc caaattggtc cgtgtggtag ttgagatgct gccttaaaat 600
tctgctcggt catcctgcct tcgcattcac tcctttcgag ctgtcgggtt cctcacgagg 660

-continued

```
cctccgggag cggattgcgc agaaaggcga cccggagaca cagagaccat acaccgacta    720

aattgcactg gacgatacgg catggcgacg acgatggcca agcattgcta cgtgattatt    780

cgccttgtca ttcagggaga aatgatgaca tgtgtgggac ggtctttaca tgggaagagg    840

gcatgaaaat aacatggcct ggcgggatgg agcgtcacac ctgtgtatgc gttcgatcca    900

caagcaactc accatttgcg tcggggcctg tctccaatct gctttaggct acttttctct    960

aatttagcct attctataca gacagagaca cacagggatc                          1000


<210> SEQ ID NO 10
<211> LENGTH: 306
<212> TYPE: DNA
<213> ORGANISM: Nannochloropsis gaditana

<400> SEQUENCE: 10

ggcactgtaa ccccggttcc gctcgacgaa ggctgggagc gccctttcgg tgggataaaa     60

tggatgcttt accgctgcgc ttcggctgag gaagagagaa atgcgagcgg ggatcggggt    120

cctagaaacg aagaaaggag aacaagttcc tggccaaaga aaaacaagac aaataccctc    180

tccaggcctg ggcccattac tttttttgc tgtttcttat acctgcactc gtgcttctct    240

agtctgtcga gaccttacct gatcttcctc cctccatcgc tccccgcccc ccccatccga    300

gcaacc                                                               306


<210> SEQ ID NO 11
<211> LENGTH: 1330
<212> TYPE: DNA
<213> ORGANISM: Artificial Sequence
<220> FEATURE:
<223> OTHER INFORMATION: SV40-ble selectable marker

<400> SEQUENCE: 11

tgcatctcaa ttagtcagca accatagtcc cgcccctaac tccgcccatc ccgcccctaa     60

ctccgcccag ttccgcccat tctccgcccc atcgctgact aatttttttt atttatgcag    120

aggccgaggc cgcctcggcc tctgagctat tccagaagta gtgaggaggc ttttttggag    180

gcctaggctt ttgcaaaaag cttgcggccg cttaagctgc agaagttggt cgtgaggcac    240

tgggcaggta agtatcaagg ttacaagaca ggtttaagga gaccaataga aactgggctt    300

gtcgagacag agaagactct tgcgtttctg ataggcacct attggtctta ctgacatcca    360

ctttgccttt ctctccacag gtgtccactc ccaggttcaa tacagctctt aagcggccgc    420

aagcttgccg ccaacatggc caagctgacc agcgccgttc cggtgctcac cgcgcgcgac    480

gtcgccggag cggtcgagtt ctggaccgac cggctcgggt tctcccggga cttcgtggag    540

gacgacttcg ccggtgtggt ccgggacgac gtgaccctgt tcatcagcgc ggtccaggac    600

caggtggtgc cggacaacac cctggcctgg gtgtgggtgc gcggcctgga cgagctgtac    660

gccgagtggt cggaggtcgt gtccacgaac ttccgggacg cctccgggcc ggccatgacc    720

gagatcggcg agcagccgtg ggggcgggag ttcgccctgc gcgacccggc cggcaactgc    780

gtgcacttcg tggccgagga gcaggactaa agatcttcta gagtcggggc ggccggccgc    840

ttcgagcaga catgataaga tacattgatg agtttggaca aaccacaact agaatgcagt    900

gaaaaaaatg ctttatttgt gaaatttgtg atgctattgc tttatttgta accattataa    960

gctgcaataa acaagttaac aacaacaatt gcattcattt tatgtttcag gttcaggggg   1020

aggtgtggga ggttttttaa agcaagtaaa acctctacaa atgtggtaaa atcgataagg   1080

atctgaacga tggagcggag aatgggcgga actgggcgga gttaggggcg ggatgggcgg   1140
```

-continued

```
agttaggggc gggactatgg ttgctgacta attgagatgc atgctttgca tacttctgcc   1200

tgctggggag cctggggact ttccacacct ggttgctgac taattgagat gcatgctttg   1260

catacttctg cctgctgggg agcctgggga ctttccacac cctaactgac acacattcca   1320

cagccatatg                                                          1330


<210> SEQ ID NO 12
<211> LENGTH: 2005
<212> TYPE: DNA
<213> ORGANISM: Artificial Sequence
<220> FEATURE:
<223> OTHER INFORMATION: GFP expression cassette with Nannochloropsis
      eIF3 promoter and terminator

<400> SEQUENCE: 12

tcataatcaa agatgagcca gccacgaagc taccggagaa ttctgtaaga aaaatgttta     60

aagttgaaaa tgctaacagt gaagtgatat cctttttttaa tggagtgttg aggtgaagtc   120

tagcatcgta ggggaaaaca ggattctgtg tcttccattc tactccttga taaagcgaag    180

aaatccgaca aaaccaaaga gattgttcaa gtttaagatt tgtaagcgta caactatgaa    240

cttcttctct ttgtaggcct gagtggtcgt atgcatacga ttcatgaagt gaatcagtat    300

cgctggattt tgcttaggag taaagcacaa ctaagaaaat atgctgcctg gcaggcatcc    360

tgagacatga ggcaagcgac gtagcaattg aatcctaatt taagccaggg catctgtatg    420

actctgttag ttaattgatg aaccaatgag ctttaaaaaa aaatcgttgc gcgtaatgta    480

gttttaattc tccgccttga ggtgcggggc catttcggac aaggttcttt ggacggagat    540

ggcagcatgt gtcccttctc caaattggtc cgtgtggtag ttgagatgct gccttaaaat    600

tctgctcggt catcctgcct tcgcattcac tcctttcgag ctgtcgggtt cctcacgagg    660

cctccgggag cggattgcgc agaaaggcga cccggagaca cagagaccat acaccgacta    720

aattgcactg gacgatacgg catggcgacg acgatggcca agcattgcta cgtgattatt    780

cgccttgtca ttcagggaga aatgatgaca tgtgtgggac ggtctttaca tgggaagagg    840

gcatgaaaat aacatggcct ggcgggatgg agcgtcacac ctgtgtatgc gttcgatcca    900

caagcaactc accatttgcg tcggggcctg tctccaatct gctttaggct acttttctct    960

aatttagcct attctataca gacagagaca cacagggatc atggagagcg acgagagcgg   1020

cctgcccgcc atggagatcg agtgccgcat caccggcacc ctgaacggcg tggagttcga   1080

gctggtgggc ggcggagagg gcaccccccga gcagggccgc atgaccaaca agatgaagag  1140

caccaaaggc gccctgacct tcagccccta cctgctgagc cacgtgatgg gctacggctt   1200

ctaccacttc ggcacctacc ccagcggcta cgagaacccc ttcctgcacg ccatcaacaa   1260

cggcggctac accaacaccc gcatcgagaa gtacgaggac ggcggcgtgc tgcacgtgag   1320

cttcagctac cgctacgagg ccggccgcgt gatcggcgac ttcaaggtga tgggcaccgg   1380

cttccccgag gacagcgtga tcttcaccga caagatcatc cgcagcaacg ccaccgtgga   1440

gcacctgcac cccatgggcg ataacgatct ggatggcagc ttcacccgca ccttcagcct   1500

gcgcgacggc ggctactaca gctccgtggt ggacagccac atgcacttca agagcgccat   1560

ccaccccagc atcctgcaga acgggggccc catgttcgcc ttccgccgcg tggaggagga   1620

tcacagcaac accgagctgg gcatcgtgga gtaccagcac gccttcaaga ccccggatgc   1680

agatgccggt gaagaataag gcactgtaac cccggttccg ctcgacgaag gctgggagcg   1740

ccctttcggt gggataaaat ggatgcttta ccgctgcgct tcggctgagg aagagagaaa   1800
```

tgcgagcggg gatcggggtc ctagaaacga agaaaggaga acaagttcct ggccaaagaa 1860
aaacaagaca aataccctct ccaggcctgg gcccattact ttttttgct gtttcttata 1920 cctgcactcg tgcttctcta gtctgtcgag accttacctg atcttcctcc ctccatcgct 1980
ccccgccccc cccatccgag caacc 2005

<210> SEQ ID NO 13
<211> LENGTH: 2697
<212> TYPE: DNA
<213> ORGANISM: Artificial Sequence
<220> FEATURE:
<223> OTHER INFORMATION: GFP expression cassette with Nannochloropsis enolase promoter and terminator

<400> SEQUENCE: 13
agcatgcgga tgacaggctt aacaaccagt attacacgtt taccgcagct cacttaccca 60
ttgttatacc caatgttacc agtactacag taatgcggtt tcgattgcgt gtggatagtg 120
ttgctgcatt tttgccggca cccggggcgg caaccatcat catcatcatc atcatggtcg 180
ttacaggatt tcttagccct ttcccacctc agccgggaaa aattgtccct ttgattgcag 240
aaattgatct tcaaatgttt tgattgtctg tcgaaacgta tgttacagta gcaggtctct 300
gagatccgta gatgcgagcc cagtgcccag aatcatgtta tcaacctcct gcaagccagg 360
ctgcagggac gtggcgggct tggacatgca tggatcttga acaacaaaac aaggtcaagc 420
tgactgcaag tctttgaaag aatagcggga taaacacagc aggtttgtac gacactacag 480
gcctcgtgaa atggccatat tcctacattc tgtgaacatc acgagattta cgatcatgct 540
tttagcgatc aagacgagtg atctgaaatc gtggagcgac acatgatgtg caacgtcgaa 600
tcccacgcac actcgtgtcg cgtcgcttaa aagctcactt cttgtaagca ctaggagaag 660
gaattgcttt ctgtgttcac cggtcacatt tcggcatggt tcgaagcggc agtgtagaag 720
tcagtgtgga tcgtaggaag ggcactata gactgagcgg cctgcccccg ccttacaaac 780
ggagccccga cgacgcatgc gccgagacga atgatggctg atcccccgta tcaggacgcg 840
tcgctcttcg tctcgtgctt gtcctgatgc cacctgaacc cgcaacacgt ccggtctaca 900
catttataca ggtcttccaa ttcctgtcga tgaggacatc gtccgctctg tgtctcctcc 960
tggggtccct ctcttactcg tcctgtacgt tgtgttttgt atggagagcg acgagagcgg 1020
cctgcccgcc atggagatcg agtgccgcat caccggcacc ctgaacggcg tggagttcga 1080
gctggtgggc ggcggagagg gcacccccga gcagggccgc atgaccaaca agatgaagag 1140
caccaaaggc gccctgacct tcagccccta cctgctgagc cacgtgatgg gctacggctt 1200
ctaccacttc ggcacctacc ccagcggcta cgagaacccc ttcctgcacg ccatcaacaa 1260
cggcggctac accaacaccc gcatcgagaa gtacgaggac ggcggcgtgc tgcacgtgag 1320
cttcagctac cgctacgagg ccggccgcgt gatcggcgac ttcaaggtga tgggcaccgg 1380
cttccccgag gacagcgtga tcttcaccga caagatcatc cgcagcaacg ccaccgtgga 1440
gcacctgcac cccatgggcg ataacgatct ggatggcagc ttcacccgca ccttcagcct 1500
gcgcgacggc ggctactaca gctccgtggt ggacagccac atgcacttca agagcgccat 1560
ccaccccagc atcctgcaga acgggggccc catgttcgcc ttccgccgcg tggaggagga 1620
tcacagcaac accgagctgg gcatcgtgga gtaccagcac gccttcaaga ccccggatgc 1680
agatgccggt gaagaataaa ttttaatcag cctacacgat gggtatgcat gaggatttga 1740
cggatcagcg cccgaggtgt gtgtgataag gcggaaatga ctctgcctat ctggcgagaa 1800

```
acggaagagt accgaaaaac agctttcgtg tgtttttgtg cgcctcacat gcggtgcatc   1860

tgcattgaga gctctgtgtt gatgtcaatg cactgtcgta tgtgtaacga ggctatattt   1920

accggaatct tgaatctcga atcgcgtgca gctctaagta cgcctcgaaa gggatgtcac   1980

tttgtagcct gcagctctca gtaggtctcg caagagatat tacttagtat tgtattctta   2040

ccgggttgtg gcaagagcgt tacgagaagg ccgtgtacga catcattgag gtgagtgaaa   2100

gtcaggattg tgctttatga tatgatgtgt ctctatacaa ccgcctggat atctagtcag   2160

gaaagataga tgaggaagac gaatcatgaa gaagtatgat acatggaaaa atgtgtactg   2220

ctcgagttct gagagctttg ttttctgctg tccatctctt gtcgttattc attgaaacat   2280

tttggcatcg ttcgtcattt tggtccacat aagtcatact tgcttcctgg tgagccatgc   2340

gtattgctgc tgcttttcag tgtacgcgca tgcaaccttt cacgtgtgca gatctccgtt   2400

acgcttccct acagccttca ctttttggct tcgaccaatt agtcacgtct caacgcgctt   2460

taaattcggc ctccgcgtat gaggcaacac atgatgcatg gctccatcca gagaggaaac   2520

ctccatccca aaaatacacc cacacttcga aacttctgtc taaattttca cggtcccaat   2580

cgcgatgctc aaagcgtagc ccactgcatc cgtgggatag ctggttctac atttgtgcac   2640

agacctcctt gtgcgccctg caccctttct attccgtgaa gtccatcctg tccacct      2697
```

<210> SEQ ID NO 14
<211> LENGTH: 1685
<212> TYPE: DNA
<213> ORGANISM: Artificial Sequence
<220> FEATURE:
<223> OTHER INFORMATION: GFP expression cassette with Nannochloropsis Rubisco accessory protein Cbbx promoter and terminator

<400> SEQUENCE: 14

```
tgcttgacgg agcgggagca agggcccgaa tcctcccaaa ctttcccctg tgcgttgtcc     60

ggtaaaagta ttaattagtt gcccggcatg agccacagcc tgccgcggta ccacctcaaa    120

acatcgcacg cgccgactcg caggggacgg cgtggtgtgg gcatcgaggg tgtctctctc    180

atcataagtg cccgcgaggc tcgcctacag cggactgcca tggcgatcct ggtcaatgca    240

tgagacgctg agacatacgc ttcctacgtg tgcagggcga tggtggacac gatgcggtac    300

cagtcgcacg tttgagggtt attgtgcctc tgtttgtggg attactcggg taccaggtgt    360

aggaaagaac gcgcgagcac ggcaacaaaa agatcttgtc ctggtctcac ccttcttctg    420

cttcatgcat actacactcc cacgcttgcg ttccattttc ggcatcataa tgcacagact    480

caaccgcata cactggaaca atggtgacga cgatggagag cgacgagagc ggcctgcccg    540

ccatggagat cgagtgccgc atcaccggca ccctgaacgg cgtggagttc gagctggtgg    600

gcggcggaga gggcaccccc gagcagggcc gcatgaccaa caagatgaag agcaccaaag    660

gcgccctgac cttcagcccc tacctgctga gccacgtgat gggctacggc ttctaccact    720

tcggcaccta ccccagcggc tacgagaacc ccttcctgca cgccatcaac aacggcggct    780

acaccaacac ccgcatcgag aagtacgagg acggcggcgt gctgcacgtg agcttcagct    840

accgctacga ggccggccgc gtgatcggcg acttcaaggt gatgggcacc ggcttccccg    900

aggacagcgt gatcttcacc gacaagatca tccgcagcaa cgccaccgtg gagcacctgc    960

accccatggg cgataacgat ctggatggca gcttcacccg caccttcagc ctgcgcgacg   1020

gcggctacta cagctccgtg gtggacagcc acatgcactt caagagcgcc atccacccca   1080

gcatcctgca gaacgggggc cccatgttcg ccttccgccg cgtggaggag gatcacagca   1140
```

acaccgagct gggcatcgtg gagtaccagc acgccttcaa gaccccggat gcagatgccg 1200
gtgaagaata atgccgatcg cgtgtagatc gtataagctt atgtgcggtc catgcttgtg 1260
cgtgatttcc cgcaatctcc atgtccacca ctacgggctg tcggagggtg tgtactcaat 1320
atttctctct ggaacgtatg tcgtgcggta ggggacgata ggggatgcgc ttgggtttgc 1380
cagatacgtg ttatcgacga tgaaagattg atacggtcaa aataattgaa cttttgtagt 1440
cgtgtagaga caagggccag ggagatagtg ggtagcgtcg cttgagctct ctttccttag 1500
acacaacgat gtccgcaagg aacaccacgg tatgtgtgat tgattggaac agcgtatggc 1560
ggaaaggaat tgaaggaccg agggaagaga gaaacgagtt tgaccaatga gggatgagct 1620
gtgatttttc cccttttgtt gcactttatt ctcatgtatg ctttctcttc gacaaaattg 1680
ttgtc 1685

<210> SEQ ID NO 15
<211> LENGTH: 1697
<212> TYPE: DNA
<213> ORGANISM: Artificial Sequence
<220> FEATURE:
<223> OTHER INFORMATION: GFP expression cassette with Nannochloropsis
Eukaryotic initiation factor 4A-III promoter and terminator

<400> SEQUENCE: 15
ggcataaagg acggcaagga aaagaaaaga aagaaagaaa aggacactta tagcatagtt 60
tgaagttata agtagtcgca atctgtgtgc agccgacaga tgcttttttt ttccgtttgg 120
caggaggtgt ggggatgtcg aagaccagtc cagctagtat ctatcctaca agtcaatcat 180
gctgcgacaa aaatttctcg cacgaggcct ctcgataaac aaaactttaa aagcacactt 240
cattgtcatg cagagtaata actcttccgc gtcgatcaat ttatcaatct ctatcatttc 300
cgcccctttc cttgcataga gcaagaaaag cgacccggat gaggataaca tgtcctgcgc 360
cagtagtgtg gcattgcctg tctctcattt acacgtactg aaagcataat gcacgcgcat 420
accaatattc ttcgtgtacg gagatgaaga gacgcgacac gtaagatcac gagaaggcga 480
gcacggttgc caatggcaga cgcgctagtc tccattatcg cgttgttcgg tagcttgctg 540
catgtcttca gtggcactat atccactctg cctcgtcttc tacacgaggg ccacatcggt 600
gcaagttcga aaaatcatat ctcaatcttc agatcctttc cagaaacggt gctcaggcgg 660
gaaagtgaag gttttctact ctagtggcta ccccaattct ctccgactgt cgcagacggt 720
ccttcgttgc gcacgcaccg cgcactacct ctgaaattcg acaaccgaag ttcaatttta 780
catctaactt ctttcccatt ctctcaccaa aagcctagct tctatggaga gcgacgagag 840
cggcctgccc gccatggaga tcgagtgccg catcaccggc accctgaacg gcgtggagtt 900
cgagctggtg ggcggcggag agggcacccc cgagcagggc cgcatgacca acaagatgaa 960
gagcaccaaa ggcgccctga ccttcagccc ctacctgctg agccacgtga tgggctacgg 1020
cttctaccac ttcggcacct accccagcgg ctacgagaac cccttcctgc acgccatcaa 1080
caacggcggc tacaccaaca cccgcatcga gaagtacgag gacggcggcg tgctgcacgt 1140
gagcttcagc taccgctacg aggccggccg cgtgatcggc gacttcaagg tgatgggcac 1200
cggcttcccc gaggacagcg tgatcttcac cgacaagatc atccgcagca acgccaccgt 1260
ggagcacctg caccccatgg gcgataacga tctggatggc agcttcaccc gcaccttcag 1320
cctgcgcgac ggcggctact acagctccgt ggtggacagc cacatgcact tcaagagcgc 1380
catccacccc agcatcctgc agaacggggg ccccatgttc gccttccgcc gcgtggagga 1440

-continued ggatcacagc aacaccgagc tgggcatcgt ggagtaccag cacgccttca agaccccgga 1500
tgcagatgcc ggtgaagaat aagagggggg ctcgagaggg agaggggtgt gtcatatgag 1560
ggcggcgggg aattcgtgtg tgaaaggaaa gcatgagtcg ataaaggggg gggtggagcg 1620
agacaaagaa gaaacggggg tcgatagcgc tgatccaaag cgtcgtctca gctttctttt 1680
ctcgcgacgc caacctc 1697

<210> SEQ ID NO 16
<211> LENGTH: 2036
<212> TYPE: DNA
<213> ORGANISM: Artificial Sequence
<220> FEATURE:
<223> OTHER INFORMATION: GFP expression cassette with Nannochloropsis Replication factor A protein 3 promoter and terminator

<400> SEQUENCE: 16
caaggattga agcgtttgtc gtactctggg tagacccaat gctcaccaac tgtcgtcttt 60
cgattgtaaa tgtgtggtaa tgacggaagg taagatgacg caaaggtgag gttgggagga 120
ggcttcagta tgagatttga ttcatcgccc ttaagaggat aaatccggga tacattcata 180
ctaatgcttg aaaaatagtt gtactcgatc acctacagta tttctccaag tttttcgtcc 240
attgacgatt ggttccagat gccacgaatc aagcctgaat cccaccccgc attatcgcat 300
ctcacctctc acctcgggca ttgcacattc cgcactctct cttgccattt tcatcccgtc 360
aggtttttag ggcgggcaat ctctgtcagg cacatttttt taataaaaag gccacatgcg 420
agtgacgcgc tatgttcgca ccggggcttc gtggcctaga tctaagtccc cccaaatatg 480
ttgtcgcctt gaccagaaag ccctttagtc cgacctcaac cacacgtaga cgggactgcg 540
gtcggtcggt cctcgtaatt atatcaagcc attttttgag cactgcaagc ttaaatttgt 600
gccgcaccgt gaaaatgatt taaaatataa ttaatcacca tattacgccc ttgaagtatt 660
ctggaatgct gttacaaagt cataatatct gaatagccga cggattggga gggctggaag 720
gtttgctcga ggcggcaaac gccaaaaagc gagaagcgcg gtctccgctc ccttcgtccc 780
gtcggggggg gggcgaggtt ctttctgcct tctggtgtgt ccgtgccgac acgaaatacg 840
atgggtggaa agcttgatcg tacaatctgg caatctataa tgtgattgtc gtcgctcaaa 900
cgtaagctct gtatctcaag aatggtccgc gcgccttctt tgggtcaccg actctctctc 960
tacctctcct cacagaaaac tcaccacaat tgtgtcggca atggagagcg acgagagcgg 1020
cctgcccgcc atggagatcg agtgccgcat caccggcacc ctgaacggcg tggagttcga 1080
gctggtgggc ggcggagagg gcacccccga gcagggccgc atgaccaaca agatgaagag 1140
caccaaaggc gccctgacct tcagccccta cctgctgagc cacgtgatgg gctacggctt 1200
ctaccacttc ggcacctacc ccagcggcta cgagaacccc ttcctgcacg ccatcaacaa 1260
cggcggctac accaacaccc gcatcgagaa gtacgaggac ggcggcgtgc tgcacgtgag 1320
cttcagctac cgctacgagg ccggccgcgt gatcggcgac ttcaaggtga tgggcaccgg 1380
cttccccgag gacagcgtga tcttcaccga caagatcatc cgcagcaacg ccaccgtgga 1440
gcacctgcac cccatgggcg ataacgatct ggatggcagc ttcacccgca ccttcagcct 1500
gcgcgacggc ggctactaca gctccgtggt ggacagccac atgcacttca agagcgccat 1560
ccaccccagc atcctgcaga acgggggccc catgttcgcc ttccgccgcg tggaggagga 1620
tcacagcaac accgagctgg gcatcgtgga gtaccagcac gccttcaaga ccccggatgc 1680
agatgccggt gaagaataaa gtccgggtaa ccagaggacg tggcatgtag acaagcacgt 1740

-continued

```
tcattttcat atacatgggc aacgaaggag agaggtctgg tggtagagtg gtagagcaaa   1800

agaggaaagc atgaaatgaa ctgtagggag tcggaaaaac aaatttgcga acaaaccacg   1860

taaacaaaga agctggtcaa gaagtcgcca tgaatccttt gatagacgct aatacgggca   1920

agcggacaag aacttgtcct catttttccc agctgtgtgg tatgattggc caatgaggtc   1980

caaatctctg attgggcctc atgaagcccc atgtcgtaaa gcttgtgtcg ctcctt       2036
```